US012318090B2

(12) United States Patent
Johnson et al.

(10) Patent No.: US 12,318,090 B2
(45) Date of Patent: *Jun. 3, 2025

(54) AORTIC FLOW METER AND PUMP FOR PARTIAL-AORTIC OCCLUSION

(71) Applicants: The Regents of the University of California, Oakland, CA (US); Government of the United States as Represented by the Secretary of the Air Force, Wright-Patterson AFB, OH (US)

(72) Inventors: Michael Austin Johnson, Sacramento, CA (US); Timothy K. Williams, Travis AFB, CA (US); Lucas Paul Neff, Decatur, GA (US)

(73) Assignees: THE REGENTS OF THE UNIVERSITY OF CALIFORNIA, Oakland, CA (US); GOVERNMENT OF THE UNITED STATES AS REPRESENTED BY THE SECRETARY OF THE AIR FORCE, Wright-Patterson AFB, OH (US)

( * ) Notice: Subject to any disclaimer, the term of this patent is extended or adjusted under 35 U.S.C. 154(b) by 197 days.

This patent is subject to a terminal disclaimer.

(21) Appl. No.: 18/160,248

(22) Filed: Jan. 26, 2023

(65) Prior Publication Data

US 2023/0414220 A1 Dec. 28, 2023

Related U.S. Application Data

(63) Continuation of application No. 16/657,588, filed on Oct. 18, 2019, now Pat. No. 11,596,411, which is a
(Continued)

(51) Int. Cl.
A61B 17/12 (2006.01)
A61B 17/00 (2006.01)
A61M 25/10 (2013.01)

(52) U.S. Cl.
CPC .. A61B 17/12036 (2013.01); A61B 17/12109 (2013.01); A61B 17/12136 (2013.01);
(Continued)

(58) Field of Classification Search
CPC ........ A61B 17/12036; A61B 17/12109; A61B 17/12136; A61B 2017/00022;
(Continued)

(56) References Cited

U.S. PATENT DOCUMENTS 2,156,289 A 5/1939 Hoy
3,467,101 A 9/1969 Raible et al.
(Continued)

FOREIGN PATENT DOCUMENTS

AU 2014223477 B2 9/2014
AU 2014223556 B2 9/2014
(Continued)

OTHER PUBLICATIONS

Holcomb et al., "Causes of death in US Special Operations Forces in the global war on terrorism: 2001-2004," Annals of Surgery, vol. 245, No. 6, pp. 986-991 (2007).
(Continued)

Primary Examiner — Sarah A Long
Assistant Examiner — Raihan R Khandker
(74) Attorney, Agent, or Firm — MARSHALL, GERSTEIN & BORUN LLP

(57) ABSTRACT

Systems and methods for partial aortic occlusion are provided. The system may include a catheter having an expandable aortic blood flow regulation device disposed on the distal end of the catheter for placement within an aorta of a
(Continued)

patient, and a catheter controller unit that causes the device to expand and contract to restrict blood flow through the aorta. The system also may include sensors for measuring blood pressure distal and proximal to the expandable device. The system further may include non-transitory computer readable media having instructions stored thereon, wherein the instructions, when executed by a processor coupled to the sensors, cause the processor to estimate aortic blood flow based on the measured blood pressures and corresponding waveforms, compare the estimated aortic blood flow with a target aortic blood flow range, generate an alert if the estimated aortic blood flow falls outside the target aortic blood flow range, and cause the catheter controller unit to adjust expansion and contraction of the expandable device to adjust an amount of blood flow through the aorta if the estimated aortic blood flow falls outside the target aortic blood flow range.

24 Claims, 13 Drawing Sheets

Related U.S. Application Data continuation of application No. PCT/US2018/028694, filed on Apr. 20, 2018.

(60) Provisional application No. 62/488,625, filed on Apr. 21, 2017.

(52) U.S. Cl.
CPC .................. *A61M 25/10182* (2013.11); *A61B 2017/00022* (2013.01); *A61B 2017/00119* (2013.01); *A61B 2017/00199* (2013.01); *A61B 2017/00221* (2013.01); *A61M 2205/18* (2013.01); *A61M 2205/3334* (2013.01); *A61M 2205/50* (2013.01); *A61M 2205/502* (2013.01); *A61M 2205/52* (2013.01); *A61M 2210/127* (2013.01); *A61M 2230/04* (2013.01); *A61M 2230/30* (2013.01); *A61M 2230/42* (2013.01); *A61M 2230/50* (2013.01)

(58) Field of Classification Search
CPC ........... A61B 2017/00119; A61B 2017/00199; A61B 2017/00221
See application file for complete search history.

(56) References Cited

U.S. PATENT DOCUMENTS

| | | | |
|---|---|---|---|
| 3,791,374 A | 2/1974 | Guarino | |
| 4,396,385 A | 8/1983 | Kelly et al. | |
| 4,464,172 A | 8/1984 | Lichtenstein | |
| 4,691,708 A | 9/1987 | Kane | |
| 4,713,888 A | 12/1987 | Broselow | |
| 4,777,951 A | 10/1988 | Cribier et al. | |
| 4,823,469 A | 4/1989 | Broselow | |
| 4,846,174 A | 7/1989 | Willard et al. | |
| 4,865,549 A | 9/1989 | Sonsteby | |
| 4,926,885 A | 5/1990 | Hinkle | |
| 4,983,166 A | 1/1991 | Yamawaki | |
| 5,047,045 A | 9/1991 | Arney et al. | |
| 5,087,246 A | 2/1992 | Smith | |
| 5,135,494 A | 8/1992 | Engelson et al. | |
| 5,152,776 A | 10/1992 | Pinchuk | |
| 5,158,529 A | 10/1992 | Kanai | |
| 5,169,386 A | 12/1992 | Becker et al. | |
| 5,217,456 A | 6/1993 | Narciso, Jr. | |
| 5,282,479 A | 2/1994 | Havran | |
| 5,320,605 A | 6/1994 | Sahota | |
| 5,344,398 A | 9/1994 | Hara | |
| 5,383,856 A | 1/1995 | Bersin | |
| 5,447,503 A | 9/1995 | Miller | |
| 5,486,192 A | 1/1996 | Walinsky et al. | |
| 5,505,702 A | 4/1996 | Arney | |
| 5,522,400 A | 6/1996 | Williams | |
| 5,558,644 A | 9/1996 | Boyd et al. | |
| 5,571,093 A | 11/1996 | Cruz et al. | |
| 5,607,394 A | 3/1997 | Andersen et al. | |
| 5,678,570 A * | 10/1997 | Manning ............. | A61M 1/3621 604/4.01 |
| 5,718,678 A | 2/1998 | Fleming, III | |
| 5,738,652 A | 4/1998 | Boyd et al. | |
| 5,779,731 A | 7/1998 | Leavitt | |
| 5,911,702 A | 6/1999 | Romley et al. | |
| 6,011,988 A | 1/2000 | Lynch et al. | |
| 6,013,019 A | 1/2000 | Fischell | |
| 6,042,532 A | 3/2000 | Freed et al. | |
| 6,102,930 A | 8/2000 | Simmons, Jr. | |
| 6,113,579 A | 9/2000 | Eidenschink et al. | |
| 6,146,370 A | 11/2000 | Barbut | |
| 6,161,547 A | 12/2000 | Barbut | |
| 6,165,199 A | 12/2000 | Barbut | |
| 6,190,304 B1 | 2/2001 | Downey et al. | |
| 6,190,356 B1 | 2/2001 | Bersin | |
| 6,231,551 B1 | 5/2001 | Barbut | |
| 6,231,572 B1 | 5/2001 | Hart et al. | |
| 6,248,083 B1 | 6/2001 | Smith et al. | |
| 6,248,121 B1 | 6/2001 | Nobles | |
| 6,254,569 B1 | 7/2001 | O'Donnell et al. | |
| 6,280,434 B1 | 8/2001 | Kinoshita et al. | |
| 6,315,768 B1 | 11/2001 | Wallace | |
| 6,394,977 B1 | 5/2002 | Taylor et al. | |
| 6,423,031 B1 | 7/2002 | Donlon | |
| 6,453,572 B2 | 9/2002 | Cross et al. | |
| 6,565,552 B1 | 5/2003 | Barbut | |
| 6,575,932 B1 | 6/2003 | O'Brien et al. | |
| 6,579,221 B1 | 6/2003 | Peterson | |
| 6,592,557 B2 | 7/2003 | Barbut | |
| 6,602,270 B2 | 8/2003 | Leschinsky et al. | |
| 6,620,128 B1 | 9/2003 | Simhambhatla | |
| 6,635,046 B1 | 10/2003 | Barbut | |
| 6,656,153 B1 | 12/2003 | Sakai et al. | |
| 6,666,814 B2 | 12/2003 | Downey et al. | |
| 6,669,679 B1 | 12/2003 | Savage et al. | |
| 6,679,860 B2 | 1/2004 | Stiger | |
| 6,695,811 B2 | 2/2004 | Samson et al. | |
| 6,712,806 B2 | 3/2004 | St. Germain et al. | |
| 6,719,270 B2 | 4/2004 | Ozawa | |
| 6,719,720 B1 | 4/2004 | Voelker et al. | |
| 6,733,513 B2 | 5/2004 | Boyle et al. | |
| 6,735,532 B2 | 5/2004 | Freed et al. | |
| 6,736,790 B2 | 5/2004 | Barbut et al. | |
| 6,743,196 B2 | 6/2004 | Barbut et al. | |
| 6,746,462 B1 | 6/2004 | Selmon et al. | |
| 6,767,345 B2 | 7/2004 | St. Germain et al. | |
| 6,796,959 B2 | 9/2004 | Davis et al. | |
| 6,796,992 B2 | 9/2004 | Barbut | |
| 6,848,448 B1 | 2/2005 | St. Germain et al. | |
| 6,868,739 B1 | 3/2005 | Krivitski et al. | |
| 6,936,056 B2 | 8/2005 | Nash et al. | |
| 6,979,318 B1 | 12/2005 | McDonald et al. | |
| 7,166,097 B2 | 1/2007 | Barbut | |
| 7,229,403 B2 | 6/2007 | Schock et al. | |
| 7,341,571 B1 | 3/2008 | Harris et al. | |
| 7,434,326 B2 | 10/2008 | Gifford | |
| 7,468,027 B2 | 12/2008 | Barbut et al. | |
| 7,503,904 B2 | 3/2009 | Choi | |
| 7,503,909 B2 | 3/2009 | Kusu et al. | |
| 7,763,043 B2 | 7/2010 | Goodin et al. | |
| 7,867,195 B2 | 1/2011 | Barbut et al. | |
| 7,888,740 B2 | 2/2011 | Tsutsumi et al. | |
| 7,892,469 B2 | 2/2011 | Lim et al. | |
| 7,909,810 B2 | 3/2011 | Noone | |
| 7,927,346 B2 | 4/2011 | VanCamp et al. | |
| 7,951,186 B2 | 5/2011 | Eidenschink et al. | |
| 7,951,819 B2 | 5/2011 | Niculescu-Duyaz et al. | |
| 7,959,644 B2 | 6/2011 | Shriver | |
| 7,993,324 B2 | 8/2011 | Barbut | |

(56) References Cited

U.S. PATENT DOCUMENTS

| | | |
|---|---|---|
| 8,088,103 B2 | 1/2012 | Teeslink et al. |
| 8,088,121 B2 | 1/2012 | Nishide et al. |
| 8,162,879 B2 | 4/2012 | Hattangadi et al. |
| 8,241,241 B2 | 8/2012 | Evans et al. |
| 8,262,611 B2 | 9/2012 | Teeslink et al. |
| 8,419,648 B2 | 4/2013 | Corl et al. |
| 8,430,899 B2 | 4/2013 | Dae et al. |
| 8,499,681 B2 | 8/2013 | Kanner et al. |
| 8,545,382 B2 | 10/2013 | Suzuki et al. |
| 8,628,461 B2 | 1/2014 | Mohl |
| 8,655,798 B2 | 2/2014 | Humphrey et al. |
| 8,672,868 B2 | 3/2014 | Simons |
| 8,672,930 B2 | 3/2014 | Wittenberger |
| 8,747,358 B2 | 6/2014 | Trombley, III et al. |
| 8,790,297 B2 | 7/2014 | Bromander et al. |
| 8,814,900 B2 | 8/2014 | Fleming, III |
| 8,888,740 B2 | 11/2014 | Barbut et al. |
| 8,900,214 B2 | 12/2014 | Nance et al. |
| 8,948,848 B2 | 2/2015 | Merhi |
| 8,951,565 B2 | 2/2015 | McCarthy |
| 8,961,426 B2 | 2/2015 | Martin et al. |
| 9,108,000 B2 | 8/2015 | Kassab |
| 9,131,874 B2 | 9/2015 | Eliason et al. |
| D748,257 S | 1/2016 | Franklin |
| 9,393,384 B1 | 7/2016 | Kapur et al. |
| 9,402,952 B2 | 8/2016 | Beyersdorf |
| 9,414,843 B2 | 8/2016 | Pavcnik et al. |
| 9,474,882 B2 | 10/2016 | Franklin |
| 9,492,084 B2 | 11/2016 | Behar et al. |
| 9,682,217 B2 | 6/2017 | Franklin et al. |
| 9,687,333 B2 | 6/2017 | Angel et al. |
| 10,004,622 B2 | 6/2018 | Sanati et al. |
| 10,111,669 B2 | 10/2018 | Eliason et al. |
| 10,143,789 B2 | 12/2018 | Frost |
| 10,149,962 B2 | 12/2018 | Franklin |
| 10,188,345 B2 | 1/2019 | Venkatraman et al. |
| 10,232,142 B2 | 3/2019 | Franklin |
| 10,279,094 B2 | 5/2019 | Williams et al. |
| 10,279,152 B2 | 5/2019 | Kapur et al. |
| 10,335,152 B2 | 7/2019 | Barbut et al. |
| 10,368,872 B2 | 8/2019 | Franklin |
| 10,569,062 B2 | 2/2020 | Franklin |
| 10,758,715 B2 | 9/2020 | Kapur et al. |
| 10,765,841 B2 | 9/2020 | Zhadkevich |
| 10,806,903 B2 | 10/2020 | Franklin et al. |
| 10,842,975 B2 | 11/2020 | Kapur et al. |
| 10,881,770 B2 | 1/2021 | Tuval et al. |
| 10,885,813 B2 | 1/2021 | Krummenacher et al. |
| 11,013,515 B2 | 5/2021 | Zhadkevich |
| 11,058,864 B2 | 7/2021 | Frost |
| 11,135,408 B2 | 10/2021 | Schwartz et al. |
| 11,154,690 B2 | 10/2021 | Avneri et al. |
| 11,253,264 B2 | 2/2022 | Franklin et al. |
| 11,311,365 B2 | 4/2022 | Zhadkevich |
| 11,464,703 B2 | 10/2022 | Johnson et al. |
| 11,596,411 B2 | 3/2023 | Johnson et al. |
| 11,602,592 B2 | 3/2023 | Johnson et al. |
| 11,633,192 B2 | 4/2023 | Johnson et al. |
| 11,672,951 B2 | 6/2023 | Franklin et al. |
| 11,857,737 B2 | 1/2024 | Franklin et al. |
| 2002/0007146 A1 | 1/2002 | Omaleki et al. |
| 2002/0062119 A1 | 5/2002 | Zadno-Azizi |
| 2002/0072647 A1 | 6/2002 | Schock et al. |
| 2002/0115982 A1 | 8/2002 | Barbut et al. |
| 2002/0193735 A1 | 12/2002 | Stiger |
| 2003/0023200 A1 | 1/2003 | Barbut et al. |
| 2003/0032974 A1 | 2/2003 | Leschinsky et al. |
| 2003/0167038 A1 | 9/2003 | Yozu et al. |
| 2003/0226568 A1 | 12/2003 | McKinley et al. |
| 2004/0073162 A1 | 4/2004 | Bleam et al. |
| 2004/0082935 A1 | 4/2004 | Lee et al. |
| 2004/0097813 A1 | 5/2004 | Williams |
| 2004/0111006 A1 | 6/2004 | Alferness et al. |
| 2004/0111016 A1 | 6/2004 | Casscells et al. |
| 2004/0254483 A1 | 12/2004 | Zdeblick et al. |
| 2004/0254528 A1 | 12/2004 | Adams et al. |
| 2005/0015048 A1 | 1/2005 | Chiu et al. |
| 2005/0059931 A1 | 3/2005 | Garrison et al. |
| 2005/0148812 A1 | 7/2005 | Nigroni et al. |
| 2005/0234293 A1 | 10/2005 | Yamamoto et al. |
| 2005/0261725 A1 | 11/2005 | Crawford et al. |
| 2006/0064059 A1 | 3/2006 | Gelfand et al. |
| 2006/0100639 A1 | 5/2006 | Levin et al. |
| 2006/0287569 A1 | 12/2006 | Schock et al. |
| 2007/0043307 A1 | 2/2007 | Raulerson et al. |
| 2007/0043409 A1 | 2/2007 | Brian, III et al. |
| 2007/0106258 A1 | 5/2007 | Chiu et al. |
| 2007/0118095 A1 | 5/2007 | Barbut |
| 2007/0129466 A1 | 6/2007 | Kagawa et al. |
| 2007/0135830 A1 | 6/2007 | Schaeffer |
| 2007/0208291 A1 | 9/2007 | Patel |
| 2007/0219441 A1 | 9/2007 | Carlin et al. |
| 2007/0219466 A1 | 9/2007 | Tremulis et al. |
| 2007/0219488 A1 | 9/2007 | Francescatti |
| 2007/0270935 A1 | 11/2007 | Newhauser et al. |
| 2008/0027356 A1 | 1/2008 | Chen et al. |
| 2008/0051764 A1 | 2/2008 | Dent et al. |
| 2008/0082046 A1 | 4/2008 | Kato et al. |
| 2008/0082119 A1 | 4/2008 | Vitullo |
| 2008/0097300 A1 | 4/2008 | Eskaros et al. |
| 2008/0178882 A1 | 7/2008 | Christopher et al. |
| 2008/0188803 A1 | 8/2008 | Jang |
| 2008/0243067 A1 | 10/2008 | Rottenberg et al. |
| 2008/0243221 A1 | 10/2008 | Arcand |
| 2008/0262477 A1 | 10/2008 | Djaladat |
| 2009/0012467 A1 | 1/2009 | Suzuki et al. |
| 2009/0026595 A1 | 1/2009 | Kadoi |
| 2009/0062666 A1 | 3/2009 | Roteliuk |
| 2009/0156978 A1 | 6/2009 | Faul et al. |
| 2009/0171222 A1 | 7/2009 | Valdes |
| 2009/0171272 A1 | 7/2009 | Tegg et al. |
| 2009/0171293 A1 | 7/2009 | Yang et al. |
| 2009/0265951 A1 | 10/2009 | Black |
| 2009/0287079 A1 | 11/2009 | Shriver |
| 2009/0312807 A1 | 12/2009 | Boudreault et al. |
| 2010/0016735 A1 | 1/2010 | Harpas et al. |
| 2010/0041984 A1 | 2/2010 | Shapland et al. |
| 2010/0113939 A1 | 5/2010 | Mashimo et al. |
| 2010/0234915 A1 | 9/2010 | Herlich et al. |
| 2010/0262076 A1 | 10/2010 | Rowe et al. |
| 2010/0268017 A1 | 10/2010 | Siess |
| 2010/0280451 A1 | 11/2010 | Teeslink et al. |
| 2010/0292635 A1 | 11/2010 | Sundar |
| 2010/0318114 A1 | 12/2010 | Pranevicius et al. |
| 2011/0034768 A1 | 2/2011 | Ozaki et al. |
| 2011/0144742 A1 | 6/2011 | Madrid et al. |
| 2011/0196412 A1 | 8/2011 | Levit et al. |
| 2011/0230821 A1 | 9/2011 | Babic |
| 2011/0295177 A1 | 12/2011 | Mohl |
| 2011/0295301 A1 | 12/2011 | Hoem et al. |
| 2011/0295302 A1 | 12/2011 | Mohl |
| 2011/0301630 A1 | 12/2011 | Hendriksen et al. |
| 2012/0101413 A1 | 4/2012 | Beetel et al. |
| 2012/0108979 A1 | 5/2012 | Franklin et al. |
| 2012/0109057 A1 | 5/2012 | Krolik et al. |
| 2012/0116352 A1 | 5/2012 | Rangi |
| 2012/0130359 A1 | 5/2012 | Turovskiy |
| 2012/0172911 A1 | 7/2012 | Welch |
| 2012/0209176 A1 | 8/2012 | Anderson |
| 2012/0215166 A1 | 8/2012 | Barki |
| 2012/0220884 A1 | 8/2012 | Yamashita et al. |
| 2012/0271231 A1 | 10/2012 | Agrawal |
| 2012/0302994 A1 | 11/2012 | Wilson et al. |
| 2013/0060316 A1 | 3/2013 | Sanati et al. |
| 2013/0102926 A1 | 4/2013 | Eliason et al. |
| 2013/0102929 A1 | 4/2013 | Haight et al. |
| 2013/0172786 A1 | 7/2013 | Olson et al. |
| 2013/0178750 A1 | 7/2013 | Sheehan et al. |
| 2013/0190619 A1 | 7/2013 | Nudel |
| 2013/0190633 A1 | 7/2013 | Dorando et al. |
| 2013/0281787 A1 | 10/2013 | Avneri et al. |
| 2013/0281869 A1 | 10/2013 | Barbut et al. |
| 2013/0289607 A1 | 10/2013 | Pedersen et al. |
| 2013/0338637 A1 | 12/2013 | Fischer, Jr. et al. |

(56) References Cited

U.S. PATENT DOCUMENTS

| | | |
|---|---|---|
| 2014/0221898 A1 | 8/2014 | Kurrus et al. |
| 2014/0243873 A1 | 8/2014 | Franklin |
| 2014/0249504 A1 | 9/2014 | Franklin et al. |
| 2014/0249573 A1 | 9/2014 | Arav |
| 2014/0316012 A1 | 10/2014 | Freyman et al. |
| 2014/0323846 A1 | 10/2014 | Niebel et al. |
| 2014/0350523 A1 | 11/2014 | Dehdashtian et al. |
| 2014/0364835 A1 | 12/2014 | Allen et al. |
| 2014/0378869 A1 | 12/2014 | Sela et al. |
| 2015/0011900 A1 | 1/2015 | Lu et al. |
| 2015/0012031 A1 | 1/2015 | Rago et al. |
| 2015/0039012 A1 | 2/2015 | Solar et al. |
| 2015/0133892 A1 | 5/2015 | Joe et al. |
| 2015/0157326 A1 | 6/2015 | Schiemanck et al. |
| 2015/0165174 A1 | 6/2015 | Helkowski et al. |
| 2015/0245867 A1 | 9/2015 | Gross |
| 2015/0272732 A1 | 10/2015 | Tilson et al. |
| 2015/0290372 A1 | 10/2015 | Muller et al. |
| 2015/0327836 A1 | 11/2015 | Stone et al. |
| 2015/0367098 A1 | 12/2015 | Aggerholm et al. |
| 2016/0000446 A1 | 1/2016 | Eliason et al. |
| 2016/0029995 A1 | 2/2016 | Navratil et al. |
| 2016/0166197 A1 | 6/2016 | Venkatraman et al. |
| 2016/0206798 A1 | 7/2016 | Williams et al. |
| 2016/0213893 A1 | 7/2016 | Franklin |
| 2016/0262647 A1 | 9/2016 | Berenfeld |
| 2016/0310103 A1 | 10/2016 | Liu et al. |
| 2016/0375230 A1 | 12/2016 | Lee et al. |
| 2017/0043123 A1 | 2/2017 | Franklin |
| 2017/0049946 A1 | 2/2017 | Kapur et al. |
| 2017/0164876 A1 | 6/2017 | Hyde et al. |
| 2017/0245794 A1 | 8/2017 | Sharma et al. |
| 2017/0266379 A1 | 9/2017 | Harrity |
| 2017/0348049 A1 | 12/2017 | Vrba et al. |
| 2017/0368313 A1 | 12/2017 | Franklin et al. |
| 2018/0064350 A1 | 3/2018 | Thakur et al. |
| 2018/0146872 A1 | 5/2018 | Shaknovich |
| 2018/0147375 A1 | 5/2018 | Johnson et al. |
| 2018/0154129 A1 | 6/2018 | Paul et al. |
| 2018/0193650 A1 | 7/2018 | Srivastava et al. |
| 2018/0228951 A1 | 8/2018 | Schwammenthal et al. |
| 2018/0236203 A1 | 8/2018 | Franklin et al. |
| 2018/0243541 A1 | 8/2018 | Kapur et al. |
| 2019/0015630 A1 | 1/2019 | Franklin et al. |
| 2019/0046762 A1 | 2/2019 | Rogers et al. |
| 2019/0046769 A1 | 2/2019 | Avneri et al. |
| 2019/0076152 A1 | 3/2019 | Franklin et al. |
| 2019/0126014 A1* | 5/2019 | Kapur ............... A61B 17/1355 |
| 2019/0290845 A1 | 9/2019 | List |
| 2019/0307462 A1 | 10/2019 | Franklin et al. |
| 2019/0336665 A1* | 11/2019 | Frost ............... A61B 5/4842 |
| 2019/0378436 A1 | 12/2019 | Krummenacher et al. |
| 2020/0038566 A1 | 2/2020 | Johnson et al. |
| 2020/0046364 A1 | 2/2020 | Johnson et al. |
| 2020/0054520 A1 | 2/2020 | Johnson et al. |
| 2020/0238018 A1 | 7/2020 | Lee et al. |
| 2020/0276419 A1 | 9/2020 | Franklin et al. |
| 2020/0329995 A1 | 10/2020 | Stone et al. |
| 2020/0375603 A1 | 12/2020 | Parekh et al. |
| 2021/0030423 A1 | 2/2021 | Starnes |
| 2021/0038229 A1 | 2/2021 | Radl et al. |
| 2021/0045864 A1 | 2/2021 | Pelssers et al. |
| 2021/0212697 A1 | 7/2021 | Frost et al. |
| 2021/0236136 A1 | 8/2021 | Mohl et al. |
| 2021/0275783 A1 | 9/2021 | Johnson et al. |
| 2021/0290243 A1 | 9/2021 | Franklin et al. |
| 2021/0322026 A1 | 10/2021 | Johnson et al. |
| 2021/0330959 A1 | 10/2021 | Frost |
| 2021/0338245 A1 | 11/2021 | Johnson et al. |
| 2021/0353298 A1 | 11/2021 | Williams et al. |
| 2021/0370025 A1 | 12/2021 | Pickering et al. |
| 2022/0323083 A1 | 10/2022 | Franklin et al. |
| 2022/0401709 A1 | 12/2022 | Beeby et al. |
| 2023/0001141 A1 | 1/2023 | Franklin et al. |
| 2023/0079117 A1 | 3/2023 | Beeby et al. |
| 2023/0138661 A1 | 5/2023 | Mohlin et al. |
| 2023/0270444 A1 | 8/2023 | Fong et al. |
| 2023/0338037 A1 | 10/2023 | Johnson et al. |
| 2023/0380702 A1 | 11/2023 | Poisner |
| 2023/0414220 A1 | 12/2023 | Johnson et al. |
| 2023/0414221 A1 | 12/2023 | Franklin et al. |
| 2024/0165380 A1 | 5/2024 | Williams et al. |

FOREIGN PATENT DOCUMENTS

| | | |
|---|---|---|
| AU | 2014317859 B2 | 3/2015 |
| AU | 2015201978 A1 | 5/2015 |
| AU | 2015274743 B2 | 12/2015 |
| AU | 2016232781 B2 | 9/2016 |
| AU | 2017272335 B2 | 12/2017 |
| CA | 2941438 | 12/2015 |
| CA | 2980018 | 9/2016 |
| CA | 2990479 | 12/2017 |
| CN | 1216929 A | 5/1999 |
| CN | 102740906 A | 10/2012 |
| CN | 105339035 A | 2/2016 |
| CN | 105792879 A | 7/2016 |
| DE | 3424552 A1 | 1/1986 |
| EM | 002688283-0001 | 3/2019 |
| EP | 0188467 A1 | 7/1986 |
| EP | 1094861 B1 | 4/2005 |
| EP | 1658808 A1 | 5/2006 |
| EP | 1911484 A2 | 4/2008 |
| EP | 2308541 A1 | 4/2011 |
| EP | 2347726 A2 | 7/2011 |
| EP | 2389974 A1 | 11/2011 |
| EP | 2716323 A1 | 4/2014 |
| EP | 2837402 A2 | 2/2015 |
| EP | 3148603 B1 | 1/2018 |
| EP | 3260158 B1 | 11/2018 |
| EP | 3270997 B1 | 7/2019 |
| EP | 3560416 A1 | 10/2019 |
| EP | 3424552 B1 | 4/2020 |
| EP | 2961464 B1 | 5/2020 |
| EP | 3549121 B1 | 9/2021 |
| FR | 2961464 A1 | 12/2011 |
| GB | 902441 A | 8/1962 |
| GB | 2297259 A | 7/1996 |
| GB | 90026882830001 | 4/2015 |
| IL | 240775 A | 11/2018 |
| JP | H03-198868 A | 8/1991 |
| JP | H03280962 A | 12/1991 |
| JP | H09-164208 A | 6/1997 |
| JP | H1080497 A | 3/1998 |
| JP | 2000217922 A | 8/2000 |
| JP | 2002505165 A | 2/2002 |
| JP | 2003079738 A | 3/2003 |
| JP | 2003535652 A | 12/2003 |
| JP | 2004533290 A | 11/2004 |
| JP | 200714820 A | 1/2007 |
| JP | 2008-237529 A | 10/2008 |
| JP | 2008546471 A | 12/2008 |
| JP | 2010538797 A | 12/2010 |
| JP | 2011055942 A | 3/2011 |
| JP | 2011245300 A | 12/2011 |
| JP | 2013042912 A | 3/2013 |
| JP | 2015120088 A | 7/2015 |
| JP | 6286564 B2 | 2/2018 |
| JP | 6343009 B2 | 6/2018 |
| JP | 6343290 B2 | 6/2018 |
| JP | 6345192 B2 | 6/2018 |
| JP | 6408176 B2 | 10/2018 |
| JP | 6472536 B2 | 2/2019 |
| WO | 92/20398 | 11/1992 |
| WO | 97/13542 | 4/1997 |
| WO | 98/34670 | 8/1998 |
| WO | 1999/24105 | 5/1999 |
| WO | 99/44666 | 9/1999 |
| WO | WO-0078386 A1 | 12/2000 |
| WO | 01/97743 A2 | 12/2001 |
| WO | 2002/085443 A1 | 10/2002 |
| WO | 2004/049970 A2 | 6/2004 |
| WO | 2006/014631 A1 | 2/2006 |
| WO | 2006/135853 A2 | 12/2006 |

(56) References Cited

FOREIGN PATENT DOCUMENTS

| | | |
|---|---|---|
| WO | 2007/001701 A1 | 1/2007 |
| WO | 2007/022592 A1 | 3/2007 |
| WO | 2008/013441 A1 | 1/2008 |
| WO | WO-2009/039203 A2 | 3/2009 |
| WO | WO-2010030882 A1 | 3/2010 |
| WO | 2010/070685 A1 | 6/2010 |
| WO | 2011/133736 A2 | 10/2011 |
| WO | 2013/096548 A1 | 6/2013 |
| WO | WO-2013096713 A2 | 6/2013 |
| WO | 2014/003809 A1 | 1/2014 |
| WO | WO-2014036530 A1 | 3/2014 |
| WO | 2014/134215 A1 | 9/2014 |
| WO | 2014/152191 A1 | 9/2014 |
| WO | WO-2014176668 A1 | 11/2014 |
| WO | 2015/006828 A1 | 1/2015 |
| WO | 2015/035393 A1 | 3/2015 |
| WO | WO-2015100393 A1 | 7/2015 |
| WO | 2015/181167 A1 | 12/2015 |
| WO | 2015/191685 A1 | 12/2015 |
| WO | WO-2016126369 A1 | 8/2016 |
| WO | 2016/149653 A2 | 9/2016 |
| WO | WO-2016/145163 A1 | 9/2016 |
| WO | WO-2016196837 A1 | 12/2016 |
| WO | 2017/210584 A1 | 12/2017 |
| WO | WO-2018089837 A1 | 5/2018 |
| WO | WO-2018/132623 A1 | 7/2018 |
| WO | 2018/195507 A1 | 10/2018 |
| WO | WO-2019195323 A1 | 10/2019 |
| WO | WO-2020033372 A1 | 2/2020 |
| WO | WO-2020039083 A2 | 2/2020 |
| WO | WO-2020157648 A1 | 8/2020 |
| WO | WO-2021178937 A1 | 9/2021 |
| WO | WO-2021188602 A2 | 9/2021 |
| WO | WO-2022266397 A2 | 12/2022 |
| WO | WO-2023043513 A1 | 3/2023 |
| WO | WO-2023086344 A1 | 5/2023 |
| WO | WO-2023224679 A2 | 11/2023 |
| WO | WO-2023225110 A1 | 11/2023 |
| WO | WO-2023230630 A1 | 11/2023 |
| WO | WO-2024030319 A1 | 2/2024 |
| WO | WO-2024228736 A2 | 11/2024 |

OTHER PUBLICATIONS

Sohn et al., "Demographics, Treatment, and Early Outcomes in Penetrating Vascular Combat Trauma," Arch Surg, vol. 143, No. 8, pp. 783-787 (2008).

Fenton et al., "Comparing risks of alternative medical diagnosis using Bayesian arguments," J. Biomed. Inf., vol. 43, pp. 485-495 (2010).

Patel et al., "Bayesian Designs for Device Clinical Trials," MDG Forum, Waltham, MA., Nov. 3, 2010, downloaded from web page: <http://www.cytel.com/pdfs/PatelBayes_Devices_Slides_11.18.10.pdf>.

Guidance for the Use of Bayesian Statistics in Medical Device Clinical Trials, U.S. Department of Health and Human Services, Food and Drug Administration, Center for Devices and Radiological Health, Division of Biostatistics, Office of Surveillance and Biometrics, Feb. 5, 2010.

Sandgren et al., "The Diameter of the Common Femoral Artery in Healthy Human: Influence of Sex, Age, and Body Size," Journal of Vascular Surgery, vol. 29, No. 3, pp. 503-510 (1999).

Sam Il et al., "Blunt Traumatic Aortic Transection: Endoluminal Repair with Commercially Available Aortic Cuffs," Journal of Vascular Surgery, vol. 38, No. 5, pp. 1132-1135 (2003).

Detrano et al. "Bayesian Probability Analysis: A Prospective Demonstration of its Clinical Utility in Diagnosing Coronary Disease," Circulation, vol. 69, No. 3, pp. 541-547 (1984).

Williams et al., "Automated Variable Aortic Control Versus Complete Aortic Occlusion In A Swine Model Of Hemorrhage", J Trauma Acute Care Surg., vol. 82, No. 4, pp. 694-703.

Johnson et al., "Small Changes, Big Effects: The Hemodynamics Of Partial And Complete Aortic Occlusion To Inform Next Generation Resuscitation Techniques And Technologies", J Trauma Acute Care Surg., vol. 82, No. 6, pp. 1106-1111.

Johnson et al., "Partial resuscitative balloon occlusion of the aorta (P-REBOA): Clinical technique and rationale", J Trauma Acute Care Surg., vol. 81, No. 5, Supplemental 1, pp. S133-S137.

Office Action mailed on Jan. 6, 2022 for CN Appl. No. 201880039616.6, 10 pages.

Notice for Reasons for Rejection mailed Jan. 31, 2022 for JP Appl. No. 2019-556882, 5 pages.

Extended European Search Report mailed on Dec. 18, 2020 for EP Application No. 18788177.6, 8 pages.

Notice of Reasons for Rejection for Japanese Patent Application No. 2023-063182, dated Mar. 21, 2024.

Communication Pursuant to Article 94(3) EPC, European Patent Application No. 18788177.6, mailed Apr. 24, 2024.

Russo et al., "Partial Resuscitative Endovascular Balloon Occlusion of the Aorta in Swine Model of Hemorrhagic Shock", *J Am Coll Surg.*, 223: 359-368 (Apr. 2016).

[Author Unknown], "Technology Pipeline". Certus Critical Care Inc. (Retrieved on Jun. 17, 2022); [Online] Retrieved from the Internet, https://www.certuscriticalcare.com/technology-portfolio, 16 pages.

Abid, Mustafa, et al., "Reperfusion repercussions: A review of the metabolic derangements following resuscitative endovascular balloon occlusion of the aorta", Journal of Trauma and Acute Care Surgery (Aug. 2020); 89(2S): S39-S44.

Adelson, P. David, et al., "Guidelines for the acute medical management of severe traumatic brain injury in infants, children, and adolescents. Chapter 1: Introduction", Pediatric Critical Care Medicine (Jul. 2003); 4(3 Suppl): S2-4.

Beyer, Carl A., et al., "Resuscitative endovascular balloon occlusion of the aorta (REBOA) in a swine model of hemorrhagic shock and blunt thoracic injury", European Journal of Trauma and Emergency Surgery (2020); 46(6): 1357-1366. Epub: Oct. 1, 2019.

Beyer, Carl A., et al., "Resuscitative endovascular balloon occlusion of the aorta induced myocardial injury is mitigated by endovascular variable aortic control", Journal of Trauma and Acute Care Surgery (Sep. 2019); 87(3): 590-598.

Bonnici, Maximilian, et al., "Successfully Stifling Retroperitoneal and Pelvic Exsanguination by Resuscitative Endovascular Balloon Occlusion of the Aorta in a Rural Setting", Journal of Endovascular Resuscitation and Trauma Management (2022); 6(2): 110-115.

Borzelli, Antonio, et al., "Successful Endovascular Embolisation of an Unusual Giant Pseudoaneurysm of the Middle Colic Artery", Journal of Endovascular Resuscitation and Trauma Management (2022); 6(2): 84-90.

Borzelli, Antonio, et al., "Successful Endovascular Management of a Massive Hemoptysis due to a Rare Oncological Giant Pulmonary Artery Pseudoaneurysm", Journal of Endovascular Resuscitation and Trauma Management (2022); 6(2): 91-96.

Certus Critical Care Presentation, "Beyond REBOA: An experimental model of Endovascular Variable Aortic Control (EVAC) using an automated extracorporeal circuit", Society for Military Surgeons' Boston (Mar. 2, 2016), 21 pages.

Certus Critical Care Presentation, "New Endovascular Techniques for Trauma: NextGenREBOA", Vienna Endovascular Trauma Meeting (Feb. 2016), 46 pages.

Chengod et al., "Selective left bronchial intubation and left-lung isolation in infants and toddlers: analysis of a new technique" J Cardiothorac Vasc Anesth. Oct. 2005; 19(5):636-641.

Chieregato, Arturo, et al., "Cerebral Blood Flow In Traumatic Contusions Is Predominantly Reduced after An Induced Acute Elevation Of Cerebral Perfusion Pressure", Neurosurgery (2007); 60(1): 115-123.

Curtis, Eleanor E., et al., "Resuscitative endovascular balloon occlusion of the aorta during non-ST elevation myocardial infarction: A case report", Trauma (2019); 21(2): 147-151.

Davidson, Anders J., et al., "A novel model of highly lethal uncontrolled torso hemorrhage in swine", Journal of Surgical Research (Oct. 2017); 218: 306-315.

(56) References Cited

OTHER PUBLICATIONS

Davidson, Anders J., et al., "Incremental balloon deflation following complete resuscitative endovascular balloon occlusion of the aorta results in steep inflection of flow and rapid reperfusion in a large animal model of hemorrhagic shock", Journal of Trauma and Acute Care Surgery (Jul. 2017); 83(1): 139-143.

Davidson, Anders J., et al., "Potential benefit of early operative utilization of low profile, partial resuscitative endovascular balloon occlusion of the aorta (P-REBOA) in major traumatic hemorrhage", Trauma Surgery & Acute Care Open (2016); 1(1): 3 pages.

Davidson, Anders J., et al., "Small Adjustments, Big Effects: Physiologic Considerations for the Clinical Implementation of Next Generation Resuscitative Balloon Occlusion of the Aorta (REBOA)", Journal of the American College of Surgeons (Oct. 2016); 223(4): e218-e219.

Davidson, Anders J., et al., "The pitfalls of resuscitative endovascular balloon occlusion of the aorta: Risk factors and mitigation strategies", Journal of Trauma and Acute Care Surgery (Jan. 2018); 84(1): 192-202.

Deaton, "Image-Guided Thrombectomy in Vascular Surgery" Endovascular Today Jul. 2005, 32-35.

Divani et al., "Blood Pressure Variability Predicts Poor In-Hospital Outcome in Spontaneous Intracerebral Hemorrhage" Stroke (2019) 50(8):2023-2029.

Dubose, Joe, "Evolving Paradigms in Vascular Injury Management", University of Maryland, Adams Crowley Shock Trauma Center (Mar. 17, 2016); 99 pages.

Extended European Search Report mailed on Dec. 18, 2020 for European Application No. 18788177.6, 8 pages.

Extended European Search Report mailed on Mar. 25, 2024 for European Application No. EP23207427.8, 13 pages.

Final Office Action for U.S. Appl. No. 17/194,053 mailed Oct. 10, 2024, 27 pages.

Final Office Action for U.S. Appl. No. 17/203,742 mailed Oct. 16, 2024, 23 pages.

Forte, Dominic M., et al., "Titrate to equilibrate and not exsanguinate! Characterization and validation of a novel partial resuscitative endovascular balloon occlusion of the aorta catheter in normal and hemorrhagic shock conditions", Journal of Trauma and Acute Care Surgery (Nov. 2019); 87(5): 1015-1025.

Forte, Dominic M., et al., "Validation of a novel partial resuscitative endovascular balloon occlusion of the aorta device in a swine hemorrhagic shock model: fine tuning flow to optimize bleeding control and reperfusion injury", Journal of Trauma and Acute Care Surgery (Jul. 2020); 89(1): 58-67.

Gantner, Dashiell, et al., "Intravenous fluids in traumatic brain injury: what's the solution?", Current Opinion in Critical Care (Aug. 2014); 20(4): 385-389.

Gerstenfeld et al., "Pulmonary vein isolation using a compliant endoscopic laser balloon ablation system in a swine model" J. Interv Card Electrophysiol (2010) 29:1-9.

Gu et al., "A new technique for sizing of atrial septal defects" Catheter Cardiovasc Interv. Jan. 1999; 46(1):51-57.

Hoareau, Guillaume L., et al., "Acute kidney injury following resuscitative endovascular balloon occlusion of the aorta: A systematic review", Journal of Endovascular Resuscitation and Trauma Management (2018); 2(2): 1-9.

Hoareau, Guillaume L., et al., "Automated partial versus complete resuscitative endovascular balloon occlusion of the aorta for the management of hemorrhagic shock in a pig model of polytrauma: a randomized controlled pilot study", Manuscript Draft submitted to Military Medicine on Mar. 6, 2020; 29 pages.

Hoareau, Guillaume L., et al., "Automated Partial Versus Complete Resuscitative Endovascular Balloon Occlusion of the Aorta for the Management of Hemorrhagic Shock in a Pig Model of Polytrauma: a Randomized Controlled Pilot Study", Military Medicine (Nov.-Dec. 2020); 185(11-12): e1923-e1930.

Hoareau, Guillaume L., et al., "Endocrine Effects of Simulated Complete and Partial Aortic Occlusion in a Swine Model of Hemorrhagic Shock", Military Medicine (May-Jun. 2019); 184(5-6): e298-e302.

Hoareau, Guillaume L., et al., "Esmolol reduces myocardial injury induced by resuscitative endovascular balloon occlusion of the aorta (REBOA) in a porcine model of hemorrhagic shock", Injury (Oct. 2020); 51(10): 2165-2171.

Hoareau, Guillaume L., et al., "Renal effects of three endoaortic occlusion strategies in a swine model of hemorrhagic shock", Injury (Nov. 2019); 50(11): 1908-1914.

International Preliminary Report on Patentability for International Application No. PCT/US2021/022644, mailed Sep. 20, 2022, 17 pages.

International Search Report and Written Opinion for Application No. PCT/US2022/033896, mailed on Nov. 28, 2022, 25 pages.

International Search Report and Written Opinion for International Application No. PCT/US2022/033898 dated Dec. 16, 2022, 30 pages.

International Search Report and Written Opinion for International Application No. PCT/US2022/049335 dated Mar. 15, 2023, 15 pages.

International Search Report and Written Opinion for International Application No. PCT/US2023/011298 dated Mar. 15, 2024, 23 pages.

Invitation to pay additional fees for International Application No. PCT/US2023/011298, dated Jan. 23, 2024, 17 pages.

Invitation to Pay Additional Fees for International Application PCT/US2022/033898, mailed Oct. 25, 2022, 21 pages.

Johnson, M. Austin, et al., "Endovascular perfusion augmentation for critical care: partial aortic occlusion for treatment of severe ischemia-reperfusion shock", Shock (May 2019); 51(5): 659-666.

Johnson, M. Austin, et al., "Letter to the Editor Re: Titrate to equilibrate and not exsanguinate!", Journal of Trauma and Acute Care Surgery (Feb. 2020); 88(2): e107-e108.

Johnson, M. Austin, et al., "Letter to the editor: Response to letter from Dr. Martin et al: Not ready for prime time: Intermittent versus partial REBOA for prolonged hemorrhage control in a highly lethal porcine injury model", Journal of Trauma and Acute Care Surgery (Jun. 2020); 88(6): e150-e151.

Johnson, M. Austin, et al., "Not ready for prime time: intermittent versus partial resuscitative endovascular balloon occlusion of the aorta for prolonged hemorrhage control in a highly lethal porcine injury model", Journal of Trauma and Acute Care Surgery (Feb. 2020); 88(2): 298-304.

Johnson, M. Austin, et al., "Response to the letter to the editor regarding: Titrate to equilibrate and not exsanguinate! Characterization and validation of a novel partial resuscitative endovascular balloon occlusion of the aorta catheter in normal and hemorrhagic shock conditions", Journal of Trauma and Acute Care Surgery (2020); 88(2): e108-e109.

Johnson, M. Austin, et al., "The effect of resuscitative endovascular balloon occlusion of the aorta, partial aortic occlusion and aggressive blood transfusion on traumatic brain injury in a swine multiple injuries model", Journal of Trauma and Acute Care Surgery (Jul. 2017); 83(1): 61-70.

Kalogeris, Theodore, et al., "Cell Biology of Ischemia/Reperfusion Injury", International Review of Cell and Molecular Biology (2012); 298: 229-317.

Kochanek, Patrick M., et al. "Guidelines for the Management of Pediatric Severe Traumatic Brain Injury, Third Edition: Update of the Brain Trauma Foundation Guidelines", Pediatric Critical Care Medicine (Mar. 2019); 20(3S): S1-S82.

Kochanek, Patrick M., et al., "Guidelines for the acute medical management of severe traumatic brain injury in infants, children, and adolescents—second edition", Pediatric Critical Care Medicine (2012); 13(1 Suppl): S1-S2.

Kuckelman et al. (2018). "Extending the golden hour for Zone 1 resuscitative endovascular balloon occlusion of the aorta: Improved survival and reperfusion injury with intermittent versus continuous resuscitative endovascular balloon occlusion of the aorta of the aorta in a porcine severe truncal hemorrhage model." J Trauma Acute Care Surg. 85(2): 318-326.

(56) References Cited

OTHER PUBLICATIONS

Leavesley, S. J. et al, "A device for performing automated balloon catheter inflation ischemia studies", Plos One (Apr. 25, 2014); 9(4): 9 pages.
Mathis et al., "Physical Characteristics of Balloon Catheter Systems Used in Temporary Cerebral Artery Occlusion" AJNR Am J Neuroradiol (1994) 15:1831-1836.
Matsumura, Yosuke, et al., "Distal pressure monitoring and titration with percent balloon volume: feasible management of partial resuscitative endovascular balloon occlusion of the aorta (P-REBOA)", European Journal of Trauma and Emergency Surgery (Nov. 6, 2019); 47(4): 1023-1029.
McGreevy, David T, et al., "EndoVascular resuscitation and Trauma Management Specialists in Training—The Future of EVTM Education", Journal of Endovascular Resuscitation and Trauma Management (2022); 6(2): 77-78.
McGreevy, David T, et al., "The Use of a Single Proglide for Large Sheath Delivery Systems", Journal of Endovascular Resuscitation and Trauma Management (2022); 6(2): 116-118.
Mundasad, Smitha, "Balloon surgery stops fatal bleeding at roadside", BBC News, Jun. 17, 2014, [online], [retrieved on unknown]. Retrieved from the Internet URL: https://www.bbc.com/news/health-27868418, 3 pages.
Nieto-Calvache, Albaro José, et al., "Technical Considerations for the Use of REBOA in the Management of Placenta Accreta Spectrum", Journal of Endovascular Resuscitation and Trauma Management (2022); 6(2): 79-83.
Non-Final Office Action for U.S. Appl. No. 18/160,248 mailed on Oct. 9, 2024, 13 pages.
Non-Final Office Action for U.S. Appl. No. 18/193,369 mailed Jul. 2, 2024, 8 pages.
Non-Final Office Action mailed on Dec. 20, 2023, for U.S. Appl. No. 17/203,742, filed Mar. 16, 2021,21 pages.
Notice of Reasons for Rejection, Japanese Patent Application No. 2021-128750, mailing date Aug. 17, 2023.
Okell et al., "A theoretical framework for quantifying blood vol. flow rate from dynamic angiographic data and application to vessel-encoded arterial spin labeling MRI" Medical Image Analysis, vol. 17, Issue 8, pp. 1025-1036, Dec. 2013.
Owens et al., "Handbook of Endovascular Peripheral Interventions" Springer (2012), 462 pages.
PCT/US2018/013413, International Preliminary Report on Patentability, mailed Jul. 16, 2019, 18 pages.
PCT/US2018/013413, International Search Report and Written Opinion mailed Apr. 4, 2018, 20 pages.
PCT/US2018/028694, International Preliminary Report on Patentability, mailed Oct. 22, 2019, 10 pages.
PCT/US2018/028694, International Search Report and Written Opinion mailed Jul. 9, 2018, 11 pages.
PCT/US2021/021264, International Preliminary Report on Patentability, mailed Sep. 6, 2022, 16 pages.
PCT/US2021/021264, International Search Report and Written Opinion mailed Jun. 2, 2021, 17 pages.
PCT/US2021/022644, International Search Report and Written Opinion mailed Oct. 7, 2021, 28 pages.
PCT/US2021/022644, Invitation to Pay Additional Fees, mailed Aug. 16, 2021, 25 pages.
PCT/US2022/033896, Invitation to Pay Additional Fees, mailed Oct. 6, 2022, 18 pages.
Peiniger, Sigune, et al., "Balanced massive transfusion ratios in multiple injury patients with traumatic brain injury", Critical Care (Feb. 22, 2011); 15(1): 1-9.
Rasmussen, Todd E., et al., "Ahead of the curve: Sustained innovation for future combat casualty care", Journal of Trauma and Acute Care Surgery 79.4 (Oct. 2015): S61-S64.
Russo, Rachel M., et al. "Two lives, one REBOA: hemorrhage control for urgent cesarean hysterectomy in a Jehovah's Witness with placenta percreta", Journal of Trauma and Acute Care Surgery (Sep. 2017); 83(3): 551-553.
Russo, Rachel M., et al., "A pilot study of chest tube versus pigtail catheter drainage of acute hemothorax in swine", Journal of Trauma and Acute Care Surgery (Dec. 2015); 79(6): 1038-1043.
Russo, Rachel M., et al., "Extending the golden hour: partial resuscitative endovascular balloon occlusion of the aorta in a highly lethal swine liver injury model", Journal of Trauma and Acute Care Surgery (Mar. 2016); 80(3): 372-380.
Russo, Rachel M., et al., "Partial resuscitative endovascular balloon occlusion of the aorta in swine model of hemorrhagic shock", Journal of the American College of Surgeons (Aug. 2016); 223(2): 359-368.
Russo, Rachel, et al., "Emerging endovascular therapies for non-compressible torso hemorrhage", Shock (2016); 46(Supplement 1): 12-19.
Saab, "Applications of High-Pressure Balloons in the Medical Device Industry" Medical Device & Diagnostic Industry Magazine Sep. 2000, 18 pages.
SAFE Study Investigators, "Saline or Albumin for Fluid Resuscitation in Patients with Traumatic Brain Injury", New England Journal of Medicine (Aug. 30, 2007); 357(9): 874-884.
Scott et al., "A novel fluoroscopy-free, resuscitative endovascular aortic balloon occlusion system in a model of hemorrhagic shock" J Trauma Acute Care Surg. Jul. 2013;75(1):122-128.
Screen capture from YouTube video clip entitled "Evolving Paradigms In Vascular Injury Management—Joseph DuBose—M.D.," 1 page, uploaded on Sep. 12, 2017; Presented on Mar. 22, 2016 by user "Surgery Grand Rounds 2016". Retrieved from Internet: https://www.youtube.com/watch?v=YfSYEM797Gg.
Shehab, Maysam, et al., "REBOA and the Open Abdomen", Journal of Endovascular Resuscitation and Trauma Management (2022); 6(2): 97-101.
Simon, Meryl A., et al., "A Case of Resuscitative Endovascular Balloon Occlusion of the Aorta (REBOA) Use in Penetrating Abdominal Aortic Injury", Journal of Endovascular Resuscitation and Trauma Management (2017); 1(1): 53-57.
Simon, Meryl A., et al., "Lower extremity cooling reduces ischemia-reperfusion injury following Zone 3 REBOA in a porcine hemorrhage model", Journal of Trauma and Acute Care Surgery (Sep. 2018); 85(3): 512-518.
Spinella, Philip C., et al., "The Association of Blood Component Use Ratios With the Survival of Massively Transfused Trauma Patients With and Without Severe Brain Injury", Journal of Trauma and Acute Care Surgery (Aug. 2011); 71(2): S343-S352.
Sugiyama, Takuya, et al., "Transcatheter Arterial Embolization for Blunt Hepatic Trauma in a Preschooler", Journal of Endovascular Resuscitation and Trauma Management (2022); 6(2): 106-109.
Sumislawski, Joshua J, et al., "Resuscitative Endovascular Balloon Occlusion of the Aorta as a Bridge to Organ Donation after Blunt Trauma", Journal of Endovascular Resuscitation and Trauma Management (2022); 6(2): 102-105.
Tibbits, Emily M., et al., "Location is everything: the hemodynamic effects of REBOA in zone 1 versus zone 3 of the aorta", Journal of Trauma and Acute Care Surgery (Jul. 2018); 85(1): 101-107.
Tsoukalas et al., "A solid-state pressure-sensing microsystem for biomedical applications" Sensors and Actuators A: Physical (1997) 62(1-3):551-555.
Weingart, Scott, MD FCCM; "Podcast 170—the ER REBOA Catheter with Joe DuBose", EMCrit Blog (Mar. 21, 2016); [Online] Accessed on Aug. 30, 2022; Retrieved from the Internet, https://emcrit.org/emcrit/er-reboa/, 3 pages.
White, Joseph M., et al., "A new pressure-regulated, partial resuscitative endovascular balloon occlusion of the aorta device achieves targeted distal perfusion", Journal of Surgical Research (Dec. 2020); (256): 171-179.
Williams et al., "Extending REBOA: Endovascular Variable Aortic Control (EVAC) in a Lethal Model of Hemorrhagic Shock", Journal of Trauma and Acute Care Surgery, vol. 81, No. 2, Aug. 2016, pp. 294-301.
Williams, Timothy K., et al., ""What's in a Name?" A Consensus Proposal for a Common Nomenclature in the Endovascular Resuscitative Management and REBOA Literature", Journal of Endovascular Resuscitation and Trauma Management (2017); 1(1): 9-12.

(56) References Cited

OTHER PUBLICATIONS

Williams, Timothy K., et al., "A novel automated endovascular variable aortic control device to expand function of standard REBOA catheters", Journal of Endovascular Resuscitation and Trauma Management (2018); 2(3): 1-8.
Williams, Timothy K., et al., "Automated variable aortic control vs. complete aortic occlusion in a swine model of hemorrhage", The Journal of Trauma and Acute Care Surgery (Apr. 2017); 82(4): 694-703.
Williams, Timothy K., et al., "Endovascular variable aortic control (EVAC) versus resuscitative endovascular balloon occlusion of the aorta (REBOA) in a swine model of hemorrhage and ischemia reperfusion injury", Journal of Trauma and Acute Care Surgery (2018); 85(3): 519-526.
Williams, Timothy Keith, et al., "Extending resuscitative endovascular balloon occlusion of the aorta: Endovascular variable aortic control in a lethal model of AQ1 hemorrhagic shock", Journal of Trauma and Acute Care Surgery (Apr. 30, 2016); 00(00): 1-8.
Examiner's Report, Canadian Patent Application No. 3,060,519, Oct. 3, 2024.
Okell, Thomas W. et al., "A theoretical framework for quantifying blood vol. flow rate from dynamic angiographic data and application to vessel-encoded arterial spin labeling MRI", Medical Image Analysis, vol. 17, Issue 8, pp. 1025-1036, Dec. 2013 (Dec. 2013), https://doi.org/10.1016/j.media.2013.06.005.

\* cited by examiner

AORTIC FLOW METER AND PUMP FOR PARTIAL-AORTIC OCCLUSION

CROSS-REFERENCE TO RELATED APPLICATION

This application is a continuation of U.S. application Ser. No. 16/657,588, filed Oct. 18, 2019, which is a continuation of International Patent Application No. PCT/US2018/028694, filed Apr. 20, 2018, which claims priority to U.S. Provisional Application No. 62/488,625, filed Apr. 21, 2017, the disclosures of which are herein incorporated by reference in their entirety for all purposes.

STATEMENT OF GOVERNMENT INTEREST

This invention was made with Government support under Grant No. HL108964 awarded by The National Institutes of Health (NIH). The Government has certain rights in the invention.

FIELD OF USE

The present disclosure relates generally to endovascular aortic flow regulation devices deployed within the aorta. More particularly, the invention relates to a precision control system and methods to achieve partial-aortic occlusion.

BACKGROUND

Hemorrhage is a leading cause of preventable death in civilian and military populations and is particularly challenging to control when arising from a non-compressible vascular injury. Death from the complications of hemorrhage from trauma and from shock continues to exist as a high probability in an overwhelming number of cases in both medical and surgical patients. Existing systems, medications, and procedures used to treat shock states frequently contribute to a patient's ultimate death through inability to maintain adequate oxygen delivery to vital organs. This delivery of oxygen is predicated on adequate blood perfusion to the organs. It is well recognized that without sufficient blood pressure to the heart and lungs hemodynamic collapse ensues resulting in decreased perfusion to the remaining organs and eventual death.

The resuscitation of a patients suffering from shock, whether neurogenic, hemorrhagic, hypovolemic, or septic, poses unique challenges especially during the early hours of critical care. Any episodes of hypotension can be detrimental to the patient. Older patients, as well as patients who have suffered a traumatic brain injury are especially susceptible to episodes of hypotension. Current practice to treat shock is dependent upon the etiology, but almost all treatment algorithms include IV fluids or blood products and, when necessary, medications that act upon the vasculature to cause vasoconstriction and an increase in blood pressure. In the setting of ongoing hemorrhage, operative control of the hemorrhage is often required to stop the bleeding.

Although the nuances of treating shock are dependent upon etiology, all treatment modalities suffer from drawbacks. First, in the setting of hemorrhage it is often not possible to stop the bleeding before the patient exsanguinates and dies from hypovolemia.

Second, in almost all forms of shock, IV fluids and or blood products are often required in large amounts early on during treatment to improve blood pressure. At times, the volume of fluid can be so great that it overwhelms the cardiovascular system resulting in pulmonary edema, ARDS, or heart failure. Therefore, although often required early on in treatment, alternative methods to remove this excess fluid are often required as soon as the patient can tolerate diuresis.

A third complication from current therapies is the secondary consequences of high doses of vasopressor medications. Vasopressors act directly on the blood vessels to increase vascular tone and improve systemic blood pressure. In the absence of a better therapeutic solution, these medications are at times necessary to improve perfusion to vital organs. However, this systemic increase in blood pressure does come at the potential cost of poor perfusion at the microvascular level. Unfortunately, due to differential responses to these medications across organs and tissue beds, unpredictable changes in regional blood flow can occur, which may ultimately have a counterproductive or detrimental effect. With high doses of these medications, certain tissues may incur permanent injury such as the distal extremities, potentially necessitating major limb amputation, or of the kidneys resulting in renal injury and the need for dialysis. In patients suffering from traumatic brain injury with increased intracranial pressure, studies in animals and in humans have demonstrated that high doses of vasopressors are often able to improve perfusion to the injured areas of the brain, but often at the expense of other regions of the brain that have such profound vasoconstriction to result in ischemic neurons.

Finally, current therapies to treat shock take time to work. Massive transfusion of blood products and boluses of IV fluids take from several minutes up to an hour to be infused, and vasopressor medications often take 10-15 minutes to begin to work and often must be titrated in doses over the subsequent hours. Even once working, some forms of shock are not responsive to single medications and multiple vasopressors are required to optimize blood pressure. These conventional therapies are frequently unable to optimize blood pressure in a timely fashion, and in many instances fail to achieve the intended target altogether. Since even short periods of ischemia can result in organ dysfunction and decreased viability, improved strategies are needed to optimize blood flow and pressure in a more timely and reliable fashion.

The ability to rapidly deliver effective blood pressure and blood flow to the heart, lungs and brain in shock states immediately before delivering blood products, crystalloids and or blood pressure medications have time to work will save innumerable lives.

The concept of using devices in the aorta to augment blood pressure is not unique. Resuscitative Endovascular Balloon Occlusion of the Aorta (REBOA) is a therapy that is used in trauma patients in extremis. REBOA has emerged as a therapy to provide temporary hemodynamic support and hemorrhage control with a balloon catheter prior to definitive surgical intervention for hemostasis. Rather than performing an emergency department thoracotomy to cross clamp the aorta to minimize distal aortic flow, a balloon catheter is completely inflated in the aorta above the level of injury to stop flow. This technology, working to completely occlude the aorta, rapidly improves blood pressure above the catheter when there is adequate circulating volume.

REBOA is now an established clinical strategy in the management of non-compressible truncal hemorrhage, providing hemodynamic support and minimizing hemorrhage. Its expanding adoption within the trauma community has been facilitated by the convergence of innovative endovascular technology and techniques with strong support from the thought leaders within the fields of vascular and trauma surgery. Despite the growing enthusiasm, it is important to recognize that REBOA produces a second physiologic insult in an already physiologically deranged patient. Specifically, the utility of REBOA is limited in its duration of use due to several adverse physiologic effects on upstream and downstream vascular beds. For example, downstream of the balloon, progressive ischemia to tissue beds distal to the point of occlusion, e.g., organ damage due to lack of blood flow, may result, and upstream of the balloon, injury to the heart, lungs, and brain due to supraphysiologic blood pressures and increased afterload proximal to the balloon may result after an extended period of time. The distal ischemia that develops in tissues below the level of occlusion limits the duration of REBOA therapy to 30-45 minutes. These side effects are greatest during Zone 1 occlusion which significantly limits the total therapeutic duration of REBOA, and subsequently, the number of patients who could benefit from this therapy as it can only be applied in a setting with a surgeon nearby capable of obtaining rapid hemorrhage control.

Therefore, is it quite feasible that deleterious consequences of sustained complete aortic occlusion will manifest with increased use of this technology. As such, the concerns regarding the progressive ischemic burden and the potential for cardiac dysfunction with complete aortic occlusion have raised the already high threshold to employ this therapy, particularly in scenarios where prolonged occlusion is required. This hesitancy on the part of providers is compounded by the fact that there is a poorly-defined tolerance threshold for REBOA, beyond which survival is not feasible. This apprehension inherently narrows the scope of REBOA, marginalizing its utility in austere or rural environments and for inter-facility transport.

A modification of the traditional REBOA technique is to utilize partial aortic occlusion with balloon catheters to provide low volume distal blood flow but not to completely stop all flow, as a method to extend duration of therapy. This technique, which has been called a variety of names including but not limited to Partial-Resuscitative Endovascular Balloon Occlusion of the Aorta (PREBOA), is a viable strategy to mitigate the effects of sustained aortic occlusion. By reducing injury below the balloon through maintaining flow, partial aortic occlusion may extend the duration of intervention, providing more time for surgical control of hemorrhage.

However, early animal experiments demonstrate that an inability to tightly regulate downstream aortic flow to injured areas during REBOA or P-REBOA can lead to early death from exsanguination. To date, the clinical efficacy of P-REBOA has been elusive because control of balloon inflation and deflation can only be accomplished by low-fidelity manipulation of the inflation syringe by hand. Current balloon technology created for complete or partial aortic occlusion to stop distal hemorrhage in the setting of trauma is unable to provide consistent titrated flow across the complete range from complete occlusion to no occlusion with manual control alone, particularly when the intent is to maintain consistent distal flow within a narrowly defined range. The ER-REBOA catheter from PryTime Medical is a compliant balloon catheter intended to decrease hemorrhage after trauma and is one such balloon that may lend itself to precision physician assisted control using an external syringe pump device.

Partial aortic occlusion may result in hemodynamic instability and ongoing hemorrhage, which limits its usefulness particularly in resource-constrained environments, due to poorly controlled distal aortic flow as described in Timothy K. Williams, M D, et al., Automated Variable Aortic Control Versus Complete Aortic Occlusion in a Swine Model of Hemorrhage (Feb. 10, 2017) (unpublished) (on file with the Journal of Trauma Acute Care Surgery), the entire contents of which is incorporated by reference herein. Accordingly, no current system allows for the estimation of aortic flow distal to a partially expanded aortic occlusion device, e.g., balloon catheters. Currently, practitioners use blood pressure proximal to the occlusion device as a surrogate marker of when partial-aortic occlusion is tolerated in trauma. Proximal blood pressure does not correlate with aortic blood flow across various levels of hemorrhage as described in M. Austin Johnson, MD, PhD, et al., Small Changes, Big Effects: The Hemodynamics of Partial and Complete Aortic Occlusion to Inform Next Generation Resuscitation Techniques and Technologies, (Jan. 5, 2017) (Journal of Trauma and Acute Care Surgery) (on file with the Journal of Trauma Acute Care Surgery), the entire contents of which is incorporated by reference herein. Thus, use of proximal blood pressure as a surrogate marker may be detrimental as proximal blood pressure is a poor marker of aortic flow and small changes in occlusion device volumes can lead to large changes in blood flow which can further lead to ongoing hemorrhage and decompensation. Specifically, proximal blood pressure lags in response to these changes in blood flow, thus making it a poor surrogate to use when attempting partial aortic occlusion. Failure to control flow at a low rate in the face of uncontrolled hemorrhage may lead to exsanguination and death. In addition, not being able to detect the flow rate may lead to unrecognized complete aortic occlusion leading to progressive ischemia. Thus, clinical application of partial aortic occlusion without having a means to estimate aortic blood flow beyond the occlusion device may be dangerous and may result in death.

In light of the aforementioned considerations and limitations of existing and proposed devices, there exists an urgent and unmet need for a viable solution to allow provide a physician with a measure of aortic flow as well as a device to assist in the control of catheter balloon volume to provide titrated distal flow.

SUMMARY

The present disclosure overcomes the drawbacks of current endovascular occlusion systems by including a series of sensors that measure patient physiology above and below the occlusion balloon as well as within the occlusion balloon to provide a measure of aortic flow past the balloon.

The system may include a catheter controller unit for automating expansion and contraction of an expandable aortic blood flow regulation device, a balloon deployed within an aorta to partially restrict blood flow through the aorta. The catheter controller unit may include a pump, e.g., syringe pump, in fluid communication with the expandable aortic blood flow regulation device via a catheter, wherein the pump may expand and contract the expandable aortic blood flow regulation device in the aorta. For example, the pump may inflate or deflate the balloon by delivering bolus volumes as small as 1 microliters, e.g., via a stepper motor.

The catheter controller unit also may include a non-transitory computer-readable media having instructions stored thereon, wherein the instructions, when executed by a processor operatively coupled to a first sensor positioned distal to the expandable aortic blood flow regulation device and a second sensor positioned proximal to the expandable aortic blood flow regulation device, cause the processor to:

receive information indicative of measured blood pressure distal to the expandable aortic blood flow regulation device from the first sensor, receive information indicative of measured blood pressure proximal to the expandable aortic blood flow regulation device from the second sensor, estimate aortic blood flow, e.g., aortic blood flow distal to the expandable aortic blood flow regulation device, based on the information from the first sensor and the information from the second sensor, compare the estimated aortic blood flow with a target aortic blood flow range, and cause the pump to adjust expansion and contraction of the expandable aortic blood flow regulation device to adjust an amount of blood flow through the aorta if the estimated aortic blood flow falls outside the target aortic blood flow range.

In one embodiment, the processor causes the catheter controller unit to adjust expansion and contraction of the expandable aortic blood flow regulation device to adjust the amount of blood flow through the aorta if the estimated aortic blood flow falls outside the target aortic blood flow range automatically based on the comparison. In another embodiment, the processor causes the catheter controller unit to adjust expansion and contraction of the expandable aortic blood flow regulation device to adjust the amount of blood flow through the aorta if the estimated aortic blood flow falls outside the target aortic blood flow range responsive to user input received via a plurality of switches and/or buttons operatively coupled to the catheter controller unit. For example, the system may include a graphical user interface that may display information indicative of the comparison, and the graphical user interface may further communicate decision support, e.g., visually or audibly, based on the comparison such that a user provides user input based on the decision support. The processor also may generate an alert if the estimated aortic blood flow falls outside the target aortic blood flow range.

The system may further include an expandable aortic blood flow regulation device disposed on the distal end portion of the catheter for placement within the aorta. The expandable aortic blood flow regulation device may expand to restrict blood flow through the aorta and to contract. The system further may include one or more sensors for measuring physiological information indicative of blood flow through the aorta. For example, a distal sensor may be disposed on the catheter distal to the expandable aortic blood flow regulation device and may measure physiological information, e.g., blood pressure in the aorta distal to the expandable aortic blood flow regulation device, and a proximal sensor may be disposed on the catheter proximal to the expandable aortic blood flow regulation device and may measure physiological information indicative, e.g., blood pressure in the aorta proximal to the expandable aortic blood flow regulation device. The one or more sensors may also measure physiological information indicative of blood flow through the aorta including at least one of pressure within the expandable aortic blood flow regulation device, heart rate, respiratory rate, blood temperature, cardiac output of the patient, carotid blood flow, pulmonary pressures, peripheral vascular resistance, or intracranial pressure. In an embodiment where two expandable aortic blood flow regulation devices are utilized, the distal sensor may be positioned distal to the expandable aortic blood flow regulation device, the proximal sensor may be positioned proximal to the second expandable aortic blood flow regulation device, and an additional sensor may be positioned in between the expandable aortic blood flow regulation device and the second expandable aortic blood flow regulation device.

In one embodiment, the system may further comprise an external central processing unit operatively coupled to the one or more sensors, e.g., the distal and proximal sensors, a sensor of the balloon catheter pressure, and the catheter controller unit. The external central processing unit may include the processor and transmit information indicative of whether the estimated aortic blood flow falls outside the target aortic blood flow range to the catheter controller unit. For example, the external central processing unit may transmit the information to the catheter controller unit via at least one of WiFi, Bluetooth, Wixel-based communication, cellular communication, or other forms of communication.

In accordance with yet another aspect of the present disclosure, a method for dynamically regulating the degree of aortic blood flow regulation for partial REBOA, partial aortic occlusion, or endovascular perfusion augmentation is provided. The method may include introducing a distal end portion of a catheter having an expandable aortic blood flow regulation device, e.g., balloon, within an aorta of a patient, expanding the expandable aortic blood flow regulation device to partially occlude blood flow through the aorta via a catheter controller unit, e.g., syringe pump, coupled to the external end portion of the catheter, measuring blood pressure distal to the expandable aortic blood flow regulation device and blood pressure proximal to the expandable aortic blood flow regulation device via one or more sensors, a sensor measuring pressure in the balloon catheter, estimating aortic blood flow based on the measured blood pressure waveforms distal and proximal to the expandable aortic blood flow regulation device and corresponding waveforms of the measured blood pressures, comparing the estimated aortic blood flow with a target aortic blood flow range, generating an alert if the estimated aortic blood flow falls outside the target aortic blood flow range, and adjusting expansion and contraction of the expandable aortic blood flow regulation device to adjust an amount of blood flow through the aorta if the estimated aortic blood flow falls outside the target aortic blood flow range. The method also may include measuring pressure within the expandable aortic blood flow regulation device. The method further may include displaying information indicative of the comparison via a graphical user interface coupled to the one or more sensors.

In one embodiment, adjusting expansion and contraction of the expandable aortic blood flow regulation device to adjust the amount of blood flow through the aorta if the estimated aortic blood flow falls outside the target aortic blood flow range is automatic. In another embodiment, adjusting expansion and contraction of the expandable aortic blood flow regulation device to adjust the amount of blood flow through the aorta if the estimated aortic blood flow falls outside the target aortic blood flow range is responsive to user input received via a plurality of switches and/or buttons operatively coupled to the catheter controller unit.

DETAILED DESCRIPTION

Figure 1:
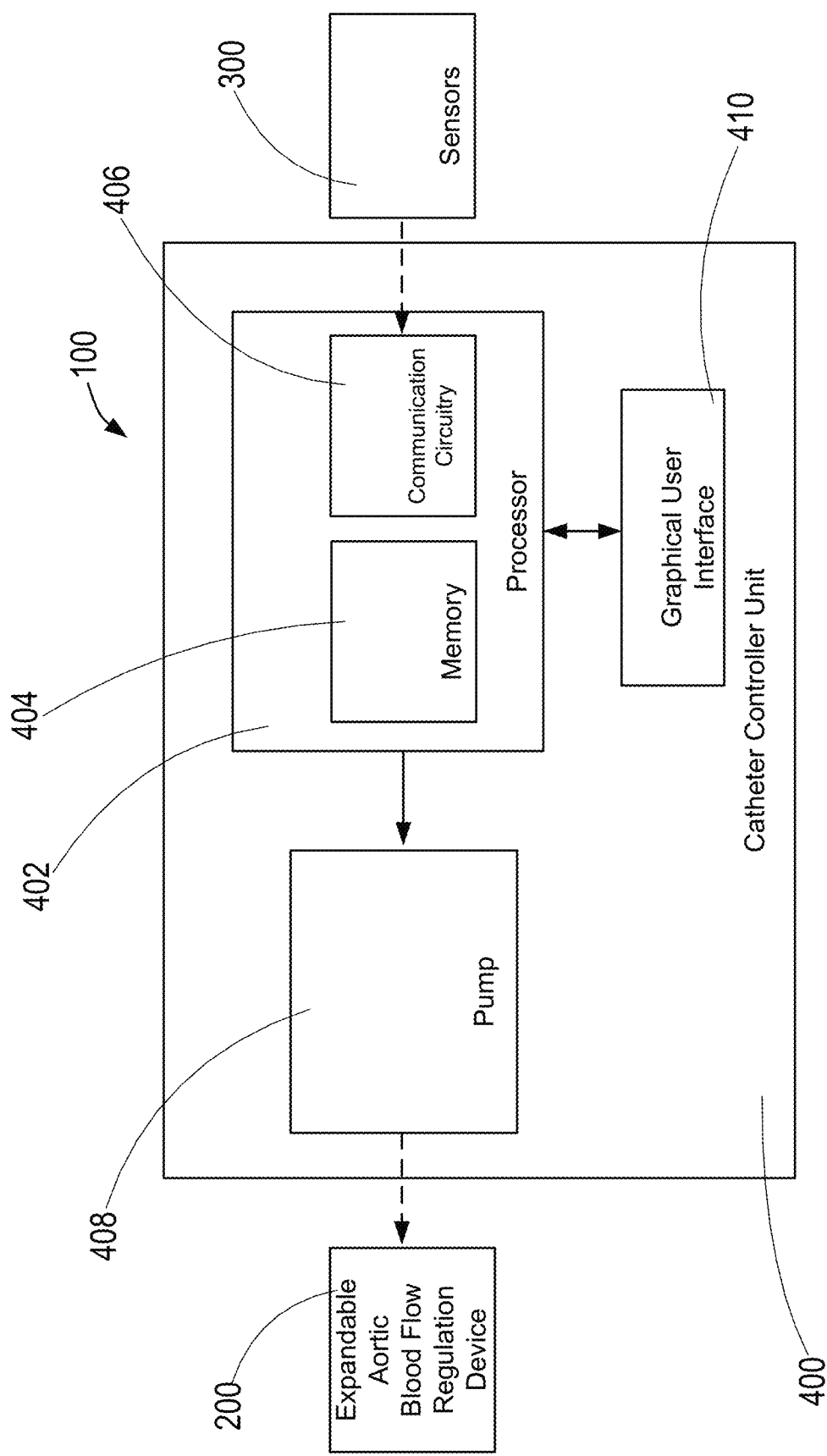
FIG. 1 is a schematic of an exemplary precision control system for partial-aortic occlusion constructed in accordance with the principles of the present disclosure.

Partial-Resuscitative Endovascular Balloon Occlusion of the Aorta (P-REBOA) is a partial-aortic occlusion platform for decreasing distal ischemia and reperfusion injury and mitigating high proximal pressure by allowing titrated controlled low-volume aortic flow distal to the site of occlusion. P-REBOA may be achieved and maintained using techniques described in M. Austin Johnson, MD, PhD, et al., *Partial Resuscitative Balloon Occlusion of the Aorta (P-REBOA): Clinical Technique and Rationale,* 80 J Trauma Acute Care Surg S133 (2016), the entire contents of which is incorporated by reference herein. Another form of partial-aortic occlusion that may be used during a variety of shock states to improve the blood pressure above the balloon is Endovascular Perfusion Augmentation for Critical Care (EPACC), which is achieved via a system comprising a series of endovascular devices, controller units for those devices, and algorithms capable of real-time changes in the EPACC devices in response to patient physiology. The concept of EPACC, in contrast to techniques such as REBOA, works via partial occlusion of the aorta similar to P-REBOA. REBOA maximizes proximal perfusion by completely occluding the aorta, at the expense of progressive ischemic injury to distal tissues. In contrast, EPACC only partially occludes the aorta, resulting in a more physiologic augmentation of proximal blood pressure. By placing the balloon at different levels within the aorta, the practitioner can select which distal capillary beds are exposed to decreased flow. Deployment of EPACC in the descending thoracic aorta results in mild reduction in blood flow to the mesentery, kidneys, liver, and extremities. In contrast, deployment at the aortic bifurcation only results in potential reduction in blood flow to the pelvis and limbs. Since aortic blood flow often exceeds what is physiologically required, minimal to moderate aortic blood flow restriction only results in minimal ischemia. This tradeoff between proximal blood pressure augmentation and distal ischemia is dependent upon the extent of shock as well as underlying patient's physiology.

The ability of partial-REBOA, partial aortic occlusion, and/or EPACC to be automated to respond dynamically to any physiologic measure makes it a viable technology to maximize perfusion in multiple shock states. Endovascular Variable Aortic Control (EVAC) utilizes automated control of aortic occlusion to precisely and dynamically regulate distal aortic flow across the full spectrum from complete occlusion to full unimpeded flow. For trauma-specific applications, the EVAC technique can be used to restrict distal aortic flow down to a very low level, striking a delicate balance between ongoing hemorrhage and progressive distal ischemia, while simultaneously augmenting proximal hemodynamics, e.g., blood flow, to the heart, lungs and brain, termed Regional Perfusion Optimization (REPO) (previously Permissive Regional Hypoperfusion). REPO is predicated on a method that can precisely and dynamically control the flow of blood to the abdominal aorta. To be clinically applicable, REPO must be accomplished with endovascular devices that can be precisely controlled. In another embodiment, these techniques may generate decision support to instruct a user and or devices to respond dynamically to any physiologic measure, thereby maximizing perfusion in multiple shock states.

REPO with EVAC has been shown to extend the duration of aortic intervention to 90 minutes in a lethal liver injury swine model, with improved survival, end organ function, and lower resuscitation requirements compared to complete aortic occlusion, e.g., REBOA. These techniques are just as viable for the treatment of impending death from exsanguination while attempting to obtain surgical control of ongoing bleeding as it is for septic shock to decrease the amount of IV fluids and vasopressors required for treatment, or neurogenic shock in the setting of traumatic brain injury or intracerebral hemorrhage. As will be understood by a person having ordinary skill in the art, the exemplary catheter controller unit described herein may be used with any commercially available P-REBOA catheter system or with custom designed catheter systems.

Referring to FIG. 1, an exemplary precision control system for partial-aortic occlusion constructed in accordance with the principles of the present disclosure is described. In FIG. 1, the components of precision control system 100 are not depicted to scale on either a relative or absolute basis. System 100 comprises catheter controller unit 400 operatively coupled to expandable blood flow regulation device 200 and sensors 300, and optionally to an external processing unit.

Catheter controller unit 400 may receive the data indicative of the measured physiological information from sensors 300, and determine whether the measured physiological information is within a predetermined target physiological range. For example, catheter controller unit 400 may receive data indicative of measured blood pressure distal to the expandable blood flow regulation device and measured blood pressure proximal to the expandable blood flow regulation device, estimate aortic blood flow based on the measured blood pressures distal and proximal to the expandable blood flow regulation device and/or from waveforms corresponding to the measured distal and proximal blood pressures, and determine whether the estimated aortic blood flow is within a predetermined target aortic blood flow range.

Catheter controller unit 400 may be coupled to expandable blood flow regulation device 200 via a catheter sized and shaped for placement within aorta A of patient P. For example, catheter controller unit 400 may be coupled to a proximal end of the catheter and expandable blood flow regulation device 200 may be disposed at the distal end of the catheter. The catheter may be any catheter well-known in the art, having a length sufficiently long such that the catheter may be inserted into a patient via the femoral artery or radial artery, and extend through the patient's vasculature into the aorta.

Following placement of a compliant aortic occlusion balloon in the aorta, e.g., blood flow regulation device 200, catheter controller unit 400 would be connected to this catheter to allow inflation or deflation to regulate aortic flow using manual control of controller unit 400 or through decision support, whereby inflation or deflation is recommended to the provider. The expandable blood flow regulation device 200 may also be any currently available balloon catheter that has not been designed for aortic occlusion and may undergo morphological changes over time.

Catheter controller unit 400 may also be coupled to expandable blood flow regulation device 200 such that catheter controller unit 400 automatically adjusts expansion and contraction of expandable blood flow regulation device 200 to adjust the amount of blood flow through the aorta if the measured physiological information falls outside the target physiological range as described in further detail below. In another embodiment, catheter controller unit 400 may be coupled to expandable blood flow regulation device 200 such that catheter controller unit 400 adjusts expansion and contraction of expandable blood flow regulation device 200 to adjust the amount of blood flow through the aorta if the measured physiological information falls outside the target physiological range, responsive to user input received by catheter controller unit 400 via, e.g., switches and/or buttons operatively coupled to catheter controller unit 400. For example, catheter controller unit 400 may generate decision support if the measured physiological information falls outside the predetermined target physiological range, which guides a user to provide user input sufficient to adjust the amount of blood flow through the aorta to bring the patient physiology within the target physiological range. Catheter controller unit 400 may expand and contract, e.g., inflate and deflate, expandable blood flow regulation device 200 in small aliquots on the order of e.g., 1 to 50 microliters. Catheter controller unit 400 may be battery powered or plugged directly into an electrical outlet.

In one embodiment, system 100 may include an external central processing unit. As described in further detail below, the external central processing unit may be operatively coupled to sensors 300 and catheter controller unit 400 such that the external central processing unit may receive the data indicative of the measured physiological information from sensors 300, determine whether the measured physiological information is within a predetermined target physiological range, calculate the amount of change of size of expandable blood flow regulation device 200 to bring the patient physiology within the target physiological range, and transmit information indicative of whether the measured physiological information falls outside the target physiological range to catheter controller unit 400 as described in further detail below. Accordingly, catheter controller unit 400 automatically adjusts expansion and contraction of expandable blood flow regulation device 200 to adjust the amount of blood flow through the aorta based on the information received from the external central processing unit. In another embodiment, catheter controller unit 400 adjusts expansion and contraction of expandable blood flow regulation device 200 to adjust the amount of blood flow through the aorta if the measured physiological information falls outside the target physiological range, responsive to user input received by catheter controller unit 400, wherein the user input is entered by a user guided by instructions generated by catheter controller unit 400 based on the information received from the external central processing unit.

Figure 2:
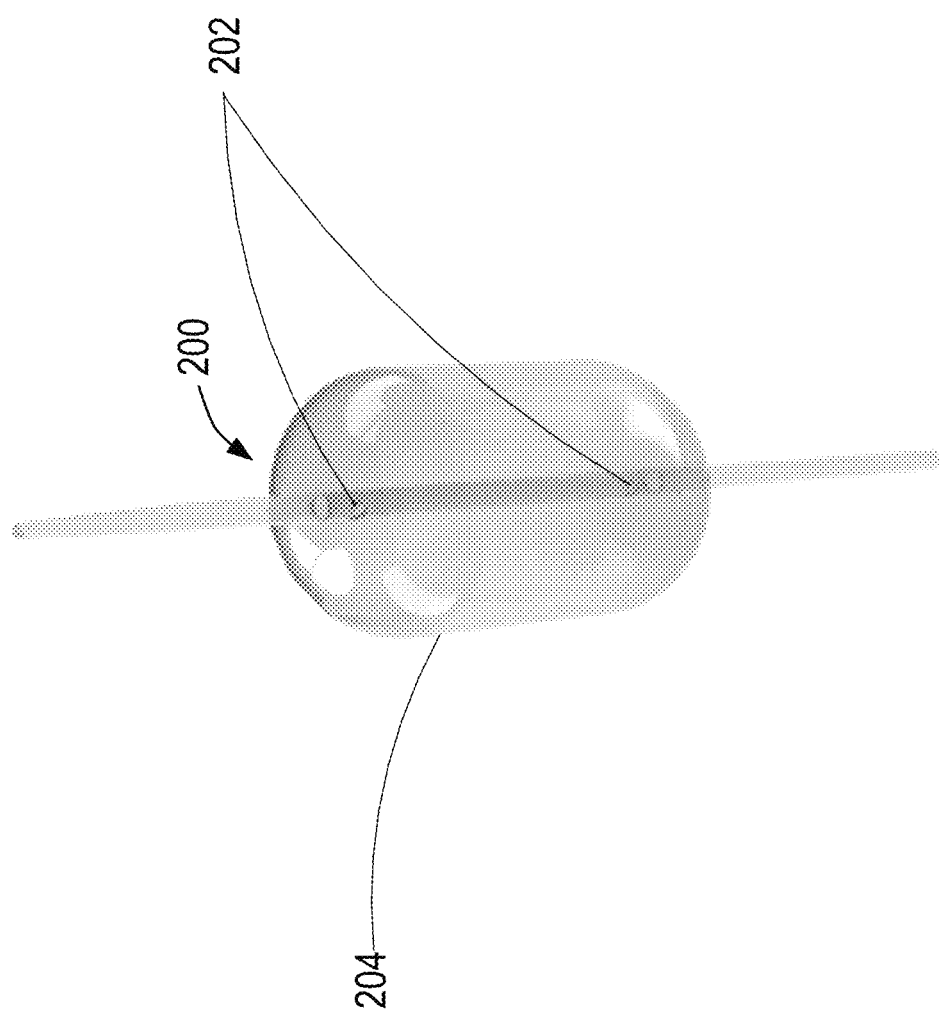
FIG. 2 illustrates an exemplary balloon catheter constructed in accordance with the principles of the present disclosure.

Referring now to FIG. 2, expandable blood flow regulation device 200 of FIG. 1 may be a balloon catheter. Accordingly, expandable blood flow regulation device 200 may include balloon 204 positioned at the distal end of the catheter. Balloon 204 is designed to be inflated to a carefully titrated balloon volume to regulate blood flow in the aorta. For example, an incompressible fluid may be introduced into balloon 204 through a lumen of the catheter via exit ports 202 such that balloon 204 may maintain the carefully titrated balloon volume. Balloon 204 may be made of a suitable membrane that will prevent diffusion of the inflation fluid across the membrane and into the vasculature of the patient. The membrane may also be designed to inflate and deflate without undergoing morphological changes over time. However, as will be understood by a person having ordinary skill in the art, expandable blood flow regulation device may be any catheter system known in the art to provide partial REBOA, aortic occlusion balloon system, or any vascular occlusion balloon system.

As expandable blood flow regulation device 200 only partially restricts blood flow in the aorta, more physiologic augmentation of proximal blood pressure may result, while simultaneously optimizing blood flow to downstream organs and tissue beds. Since aortic blood flow is greater overall than is physiologically required in the majority of cases for patient's in shock, minimal-to-moderate occlusion results in only minimal ischemia. This tradeoff between proximal blood pressure augmentation and distal ischemia is dependent upon the extent of shock as well as the patient's underlying physiology. As will be understood by a person having ordinary skill in the art, catheter controller unit 400 may be operatively coupled to any P-REBOA balloon catheter system, REBOA catheter system, aortic occlusion balloon system, or other vascular occlusion balloon system, e.g., IVC or iliac.

Figure 3:
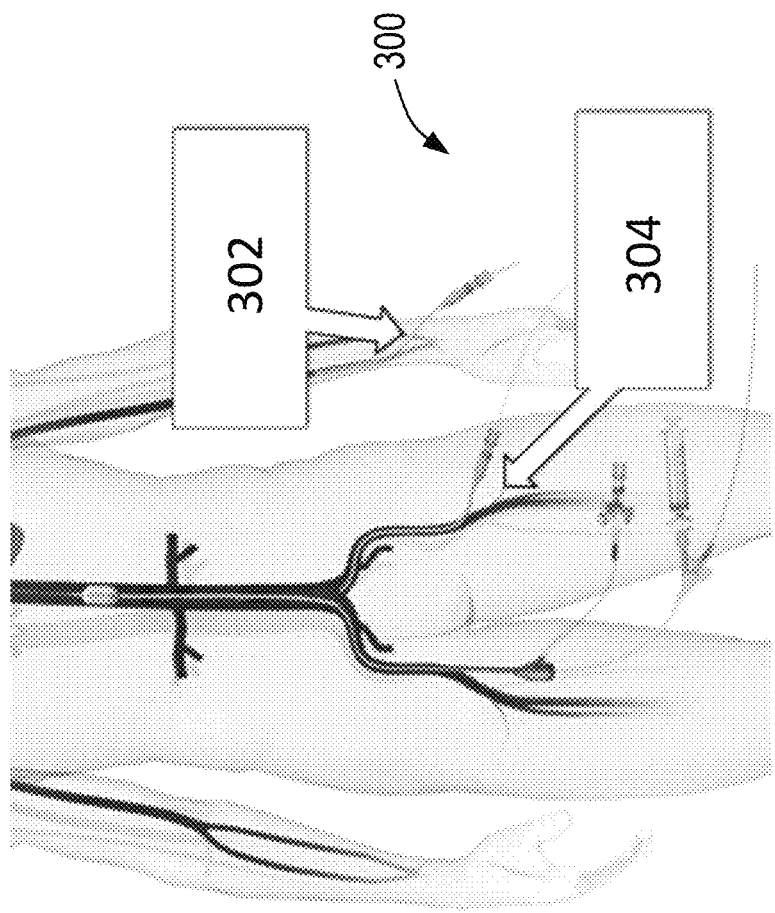
FIG. 3 illustrates the exemplary sensors of FIG. 1.

Referring now to FIG. 3, sensors 300 may measure physiological information indicative of blood flow through the aorta to determine the patient's underlying physiology. For example, sensors 300 may measure physiological parameters including, but not limited to, blood pressure distal to the expandable blood flow regulation device, blood pressure proximal to the expandable blood flow regulation device, pressure within the expandable blood flow regulation device, heart rate, respiratory rate, aortic blood flow proximal or distal to the expandable blood flow regulation device, blood temperature, cardiac output of the patient, carotid blood flow, pulmonary pressures, peripheral vascular resistance, or intracranial pressure. Sensors 300 may include one or more sensors. For example, as shown in FIG. 3, sensors 300 comprise two sensors, distal sensor 302 positioned to measure blood pressure from a blood pressure line inserted into a distal artery and sensor 304 positioned to measure blood pressure form a blood pressure line inserted into an artery proximal to the expandable blood flow regulation device. For example, distal sensor 302 may be connected, e.g., via luer lock connectors, to a flush port of an expandable blood flow regulation device introducer sheath or to an arterial line positioned in the contralateral femoral artery, and proximal sensor 304 may be connected to a proximal pressure port on the expandable blood flow regulation device or on a proximal arterial line via a radial artery. Another sensor may be connected to an inflation port of expandable blood flow regulation device 200 to measure pressure within expandable blood flow regulation device 200 to protect against over inflation and facilitate detection of loss of expandable blood flow regulation device pressure due either to poor connection or expandable blood flow regulation device leak/rupture.

Sensors 300 may record data indicative of the measured physiological information either through analog or digital mechanisms. This data may then be used to determine whether more or less restriction of aortic blood flow is required to maximize vital organ perfusion via automated augmentation of blood pressure while simultaneously aiming to control hemorrhage, mitigate ischemia below the expandable blood flow regulation device, and mitigate high pressure above the expandable blood flow regulation device, as described in further detail below.

Patient physiology may also be monitored via real-time and intermittent measures of compounds with in the patient's blood, serum, urine, or saliva, e.g., levels of lactate, levels of cortisol, levels of reactive oxygen species, the pH of the fluid, as well as other commonly used patient physiology markers.

Referring back to FIG. 1, catheter controller unit 400 includes processor 402 having memory 404 and communication circuitry 406, and pump 408. Processor 402 may be operatively coupled to sensors 300, graphical user interface 410, and pump 408, and pump 408 may be operatively coupled to expandable blood flow regulation device 200.

Processor 402 may receive data indicative of the measured physiological information from sensors 300 via communication circuitry 406, and record the data in memory 404. Processor 402 may further record waveforms corresponding to the measured physiological information from sensors 300 in memory 404. Memory 404, e.g., non-transitory computer readable media, may store a target physiological parameter and a corresponding range associated with blood flow through the aorta, and instructions that, when executed by processor 402, cause processor 402 to compare the measured physiological information with the target physiological range to determine whether the measured physiological information is within the predetermined target physiological range. Processor 402 may cause graphical user interface 410, e.g., touch enabled LCD display, to display information indicative of the comparison of the measured physiological information with the target physiological range. For example, processor 402 may receive data indicative of measured blood pressure distal to expandable blood flow regulation device 200 and measured blood pressure proximal to expandable blood flow regulation device 200, from which processor 402 may estimate aortic blood flow. Accordingly, processor 402 may cause graphical user interface 410 to display, e.g., graphically, the estimated aortic blood flow as well as the target physiological parameter, e.g., target aortic blood flow, and its desired corresponding range. For example, graphical user interface 410 may display the target aortic blood flow in the centerline with the predetermined desired range above and below the centerline, e.g., in green, wherein the desired range is surrounded by a predetermined acceptable range, e.g., in yellow, above and below the desired range, and wherein the acceptable range is surrounded by a predetermined unacceptable range, e.g., in red, above and below the acceptable range. Graphical user interface 410 may display the estimated aortic blood flow in relation to the ranges, which will indicate whether the estimated aortic blood flow falls outside the desired and/or acceptable range. As such, processor 402 may calculate an appropriate change in the amount of occlusion by expandable blood flow regulation device 200 necessary to bring the patient physiology within the target physiological range based on the current measured patient physiology.

Graphical user interface 410 may permit a user to select various menu functions, e.g., setting the target aortic flow, setting audible alarms to indicate when blood flow is deviating from the desired range, to allow for zeroing of sensors 300, to allow for entering patient information including, for example, height, weight, gender, name, and date of birth. Accordingly, memory 404 may store patient profiles corresponding to the patient information entered via graphical user interface 410. Information stored in memory 404 may be downloaded from catheter controller unit 400 via, e.g., a removable media card.

Processor 402 comprises a series of sub-algorithms for controlling each aspect of appropriate balloon inflation, deflation, and rate of response to physiologic changes when a balloon catheter is used. These individual algorithms may also calculate: initial calibration to identify the physical measurements of the vessel, determination of complete occlusion, identification of a working range of the catheter, e.g., the range of occlusion that results due to changes in patient physiology, set point optimization, weaning off from catheter-based physiologic support, and balloon volume tuning.

For balloon catheter 200, the balloon calibration sequence occurs upon initial insertion of the catheter or upon initiation of EPACC. The calibration sequence is also activated any time large changes in the hemodynamics are detected that are not induced by EPACC. Upon initiation of the balloon calibration sequence, pump 408 of catheter controller unit 400 will iteratively introduce small aliquots of gas or fluid, e.g., carbon dioxide, saline, or a mixture of contrast and saline, into the balloon. During sequential boluses, proximal physiology may be monitored until a change is observed, which denotes the low set point of the working range of balloon 204. Balloon 204 will continue to inflate until the distal blood pressure waveform is extinguished or until proximal physiologic changes are no longer observed, which denotes the upper working range of balloon catheter 200. Alternatively, the upper limit may be denoted by measuring the cessation of aortic flow. A mid-point of the working range may be set as an interval increase in balloon volume from the low set point and may be referenced for a rapid return to working range if needed during EPACC.

After balloon calibration has occurred and initial balloon volume set points have been identified, processor 402 causes catheter controller unit 400 to adjust the shape and size of expandable blood flow regulation device 200 via pump 408 to augment proximal blood pressure responsive to patient physiology. As described above, processor 402 compares the measured physiological information received from sensors 300 with the target physiological range stored in memory 404 to determine whether the measured physiological information is within the predetermined target physiological range. For example, if proximal blood pressure is set as the physiologic marker, when processor 402 determines that proximal blood pressure drops below the target blood pressure range, catheter controller unit 400 expands expandable blood flow regulation device 200 via pump 408, e.g., inflate the balloon. Similarly, when processor 402 determines that proximal blood pressure exceeds the target blood pressure range, catheter controller unit 400 contracts expandable blood flow regulation device 200 via pump 408, e.g., deflate the balloon. The amount of change in balloon volume that occurs in response to blood pressure changes that are out of range is dependent upon how far the current measured blood pressure is from the target blood pressure. Therefore, if the blood pressure is only minimally out of the target range, a small change in size of expandable blood flow regulation device 200 is made. In contrast, when the blood pressure is significantly out of the target range, a larger change in size of expandable blood flow regulation device 200 is made. Processor 402 may record the amount of change in size of expandable blood flow regulation device 200 caused by pump 408 such that memory 404 stores a running tally of, e.g., balloon filling volume. Accordingly, a user may be provided with constant real-time information indicative of, e.g., how much fluid is within the balloon.

An example algorithm that may be used to provide EPACC includes:

$$uLBolus = (P_0 - P_S)^J * V$$

where $P_0$ is current pressure, $P_S$ is set point pressure, J is a constant, and V is a constant described below. One skilled in the art will understand that alternative algorithms could be used to adjust balloon volumes based upon current and goal physiology. For example, alternative algorithms may use less or more than two constants and/or variables.

The balloon tuning algorithm allows for the magnitude of the change of size of expandable blood flow regulation device 200 in response to the difference between the measured physiological information and the target physiological parameter to be dynamic, controlled by, e.g., the constant V and J. Initially V and J may be set to a default, but V or J may change dynamically dependent upon the magnitude of physiologic changes that occur beyond the initial target set points. For example, if blood pressure is set as the physiologic marker and the initial blood pressure recorded by sensors 300 was below the set point pressure, but the resulting blood pressure recorded by sensors 300 after the change in expansion amount of expandable blood flow regulation device 200 by pump 408, V and or J would then be modified in order to correct for overshooting the goal set point. If the measured blood pressure is determined to be within the target blood pressure and as a result, the amount of expansion of expandable blood flow regulation device 200 drops below the low set point, expandable blood flow regulation device 200 will then wean off to its baseline zero set point. This may occur by deflating the balloon. For example, the following code illustrates dynamically scaling expansion of an expandable blood flow regulation device.

```
void balloon_titration ( );
void balloon_titration_correction ( );
void balloon_titration( ) // this function establishes the bolus volume that
    is delivered to the balloon based on the deviation of the
    normalized_distal_pressure from the setpoint pressure_setpoint
{
  if (elapsed timer is greater than the delay period timedelay)
  {
    Set elapsed timer to zero
    Set the variable pressure_1 = normalized_distal_pressure
    Calculate the difference between the current normalized distal
    pressure and the pressure setpoint
    pressure_difference = pressure_1 - pressure_setpoint
    Calculate the absolute value of this difference
    pressure_difference=abs (pressure_difference)
    If (pressure_difference is greater than 1mmH)
        Then perform function balloon_titration_correction( ) ;
```

-continued

```
    Read_All_Sensors ( ) :  //reads the pressure sensor values
    Set the variable pressure_0 = normalized_distal_pressure
    If (normalized_distal_pressure is less than 0.5 mmHg above or below
    the pressure_setpoint)
        Then set the delay period to minimum delay
        timedelay = 2000 msec
    Else If (normalized_distal_pressure is greater than 0.5 mmHg above
    or below the pressure_setpoint)
        Then
            Inflate balloon by volume established from equation:
            Bolus_Volume = round(((normalized_distal_pressure -
            pressure_setpoint )*scaling_factor) )
            Set for delay period established from equation:
            timedelay = 2000 msec +
            timescale*pressure_difference*timer_variable_constant
    Else If (normalized_distal_pressure is less than 0.5 mmHg above or
    below the pressure_setpoint)
        Then
            Deflate balloon by volume established from equation:
            Bolus_Volume = round(((normalized_distal_pressure -
            pressure_setpoint)*scaling_factor) )
            Set for delay period established from equation:
            timedelay = 2000 msec +
            timescale*pressure_difference*timer_variable_constant
}
void balloon_titration_correction( )  //dynamically scales balloon titration
    amount when the distance from the setpoint in greater than 1mmmHg
{
  If (pressure_0 is greater than pressure_setpoint)
  {
    If (pressure_1 is less than pressure_setpoint)
    {
      The bolus volume has overshot the target pressure, therefore the
      scaling factor v will be incremented to a small number as follows:
      Set v = v - (pressure_difference)/c
      // where c represents the volume correction constant
    }
    Else If (pressure_1 is greater than pressure_setpoint)
    {
      The bolus volume has undershot the target pressure, therefore the
      scaling factor v will be incremented to a small number as follows:
      Set v = v + (pressure_difference)/(4*c)
    }
  }
  Else If (pressure_0 is less than than pressure_setpoint
  {
    If (pressure_1 is greater than pressure_setpoint)
    {
      The bolus volume has overshot the target pressure, therefore the
      scaling factor v will be incremented to a small number as follows:
      Set v = v - (pressure_difference)/c
      where c represents the volume correction constant
      Else If (pressure_1 is less than pressure_setpoint)
    {
      The bolus volume has undershot the target pressure, therefore the
      scaling factor v will be incremented to a small number as follows:
      Set v = v + (pressure_difference)/(4*c)
    }
  }
}
```

As described above, processor 402 may automatically expand and contract expandable blood flow regulation device 200 via pump 408 in accordance with the principles of the present disclosure. For example, when expandable blood flow regulation device 200 comprises a balloon catheter, pump 408 may be a syringe pump designed to inject or remove fluid from the balloon to inflate or deflate the balloon via the exit ports in fluid communication with the lumen of the catheter. The syringe pump may make small titrated changes in balloon volume, e.g., on the order of 1 to 50 microliters, in response to patient physiology via automation. For example, the syringe pump may include a metallic threaded rod to allow linear translation of the syringe plunger guide. The syringe pump may be actuated via a low power consumption stepper motor, e.g., NEMA 11 or 8, and may contain a reduction gear box. In one embodiment, the syringe pump may be controlled via a linear actuator.

After each change in balloon volume by pump 408 of catheter controller unit 400, processor 402 may wait for a predetermined period of time for the resulting physiologic response to be monitored before further adjusting the balloon volume.

In one embodiment, pump 408 may provide for manual inflation of the balloon, e.g., when automation is either unavailable or not feasible. For example, a manual pump may include a syringe pump that may inject fluid using the normal action of a syringe, but may also inject or remove fluid via screw actuation once threads on the plunger and within the barrel of the syringe have been activated. Injection via normal syringe plunging, but fluid removal only via screw actuation allows for rapid inflation of the balloon, but carefully titrated removal of fluid based upon the pitch of the thread on the plunger. As will be understood by one having ordinary skill in the art, the manual pump may include, e.g., peristaltic pumps, rotatory pumps, etc.

In another embodiment, catheter controller unit 400 may generate decision support if the measured physiological information falls outside the predetermined target physiological range. The decision support, e.g., set of instructions, may be communicated to the user via, e.g., visually or audibly via graphical user interface 410, such that the decision support guides a user to provide user input via, e.g., graphical user interface 410 or a plurality of switches and/or buttons operatively coupled to processor 402. As will be understood by one of ordinary skill in the art, graphical user interface 410 may include a plurality of switches and/or buttons for receiving user input. The user input may be sufficient to change the amount of occlusion by expandable blood flow regulation device 200 necessary to bring the patient physiology within the target physiological range based on the current measured patient physiology as calculated by processor 402. Accordingly, in response to receiving the user input, processor 402 causes pump 408, e.g., syringe pump, to inject or remove fluid from the balloon to inflate or deflate the balloon via the exit ports in fluid communication with the lumen of the catheter. The syringe pump may make small titrated changes in balloon volume, e.g., on the order of 1 to 1000 microliters, in response to the user input.

Figure 4:
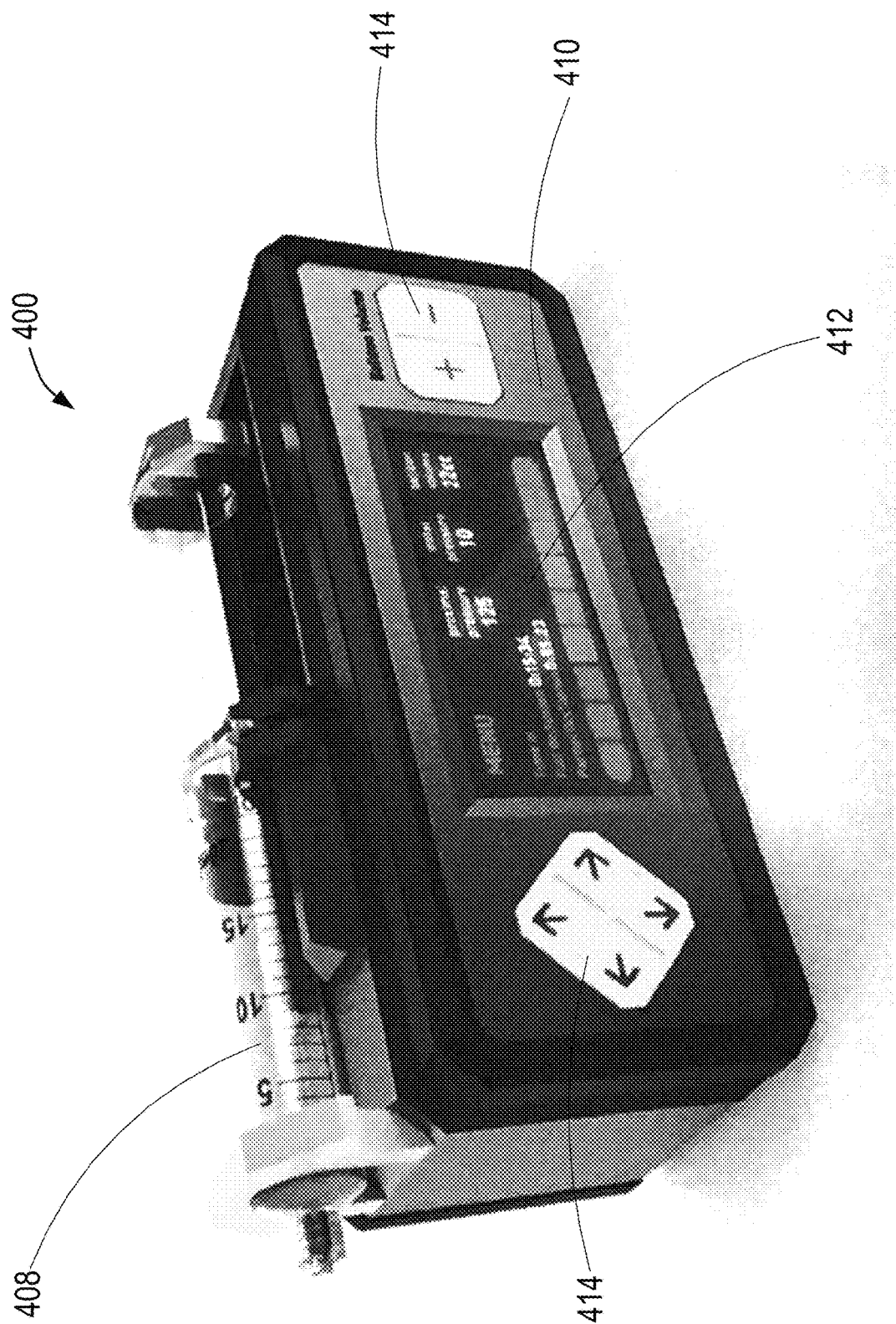
FIG. 4 is a conceptual illustration of an exemplary catheter controller unit of FIG. 1.

FIG. 4 illustrates a conceptual embodiment of catheter controller unit 400 having graphical user interface 410 and wherein pump 408 is a syringe pump. As shown in FIG. 4, graphical user interface 410 may include display 412 for visually communicating information to a user, and plurality of buttons and switches 414 for allowing a user to interact with catheter controller unit 400, e.g., expand or contract expandable blood flow regulation device 200 and/or navigate through the menu functions provided by graphical user interface 410.

Figure 5:
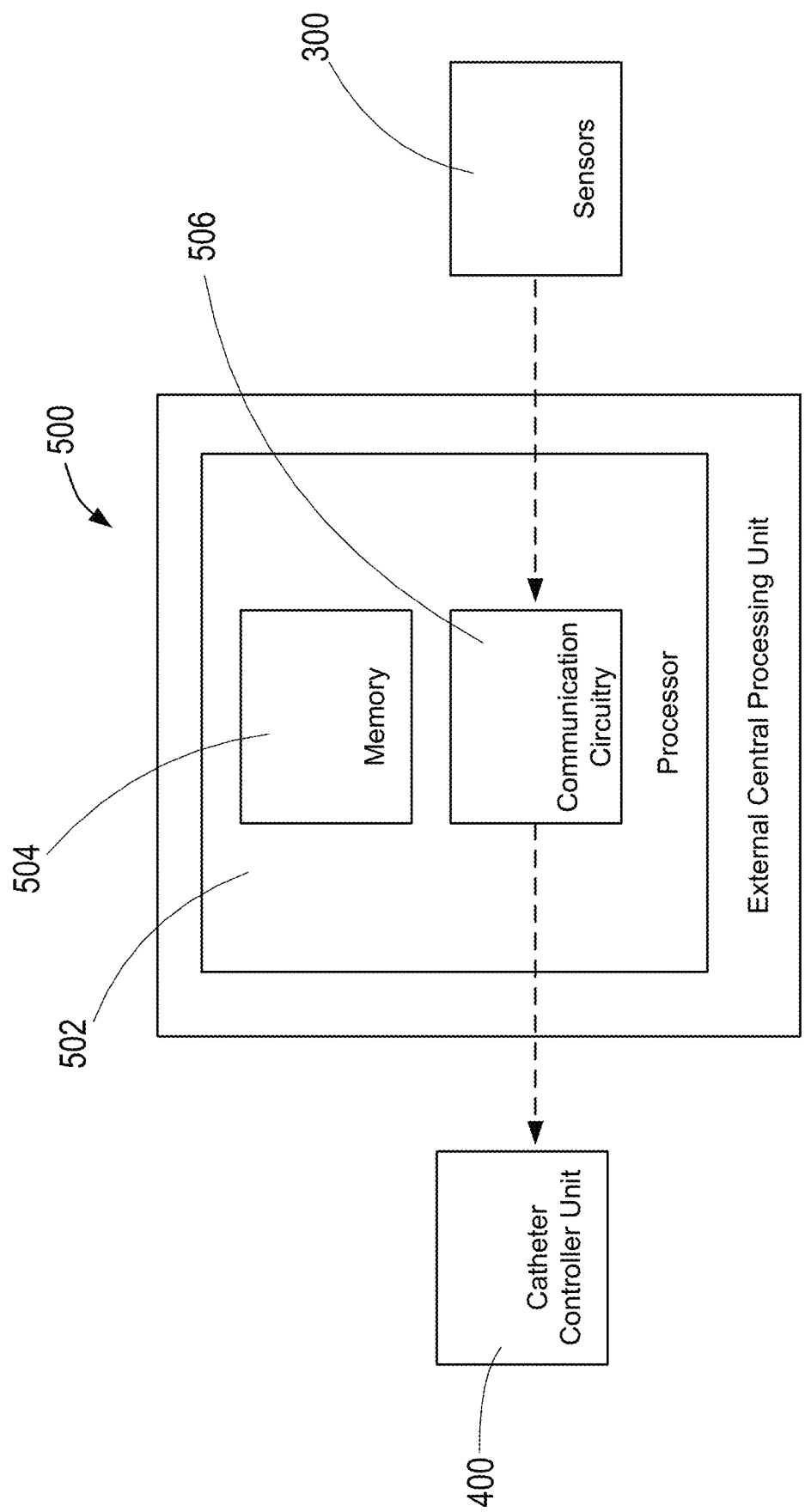
FIG. 5 is a schematic of an exemplary external central processing unit constructed in accordance with the principles of the present disclosure.

Referring to FIG. 5, an exemplary external central processing unit constructed in accordance with the principles of the present disclosure is described. As shown in FIG. 5, external central processing unit 500 comprises processor 502 having memory 504 and communication circuitry 506. In FIG. 5, components of processor 502 are not depicted to scale on either a relative or absolute basis. Processor 502 may be constructed similarly to processor 402 of catheter controller unit 400 of FIG. 1, such that processor 502 may be operatively coupled to sensors 300, receive data indicative of the measured physiological information from sensors 300, and compare the measured physiological information with a target physiological range stored in memory 504. When system 100 comprises external central processing unit 500, processor 502 of external central processing unit 500 determines whether the measured physiological information is within the target physiological range, calculates information indicative of the appropriate change in the amount of occlusion by expandable blood flow regulation device 200 required to bring the patient's physiology within the target physiological range if the measured physiological information falls outside the target physiological range, and transmits the information to catheter controller unit 400 via communication circuitry 506. For example, communication circuitry 506 of external central processing unit 500 may transmit the information to communication circuitry 406 of catheter controller unit 400 via at least one of WiFi, Bluetooth, Wixel-based communication, or cellular communication, or a wired connection, or other form of communication.

Figure 6:
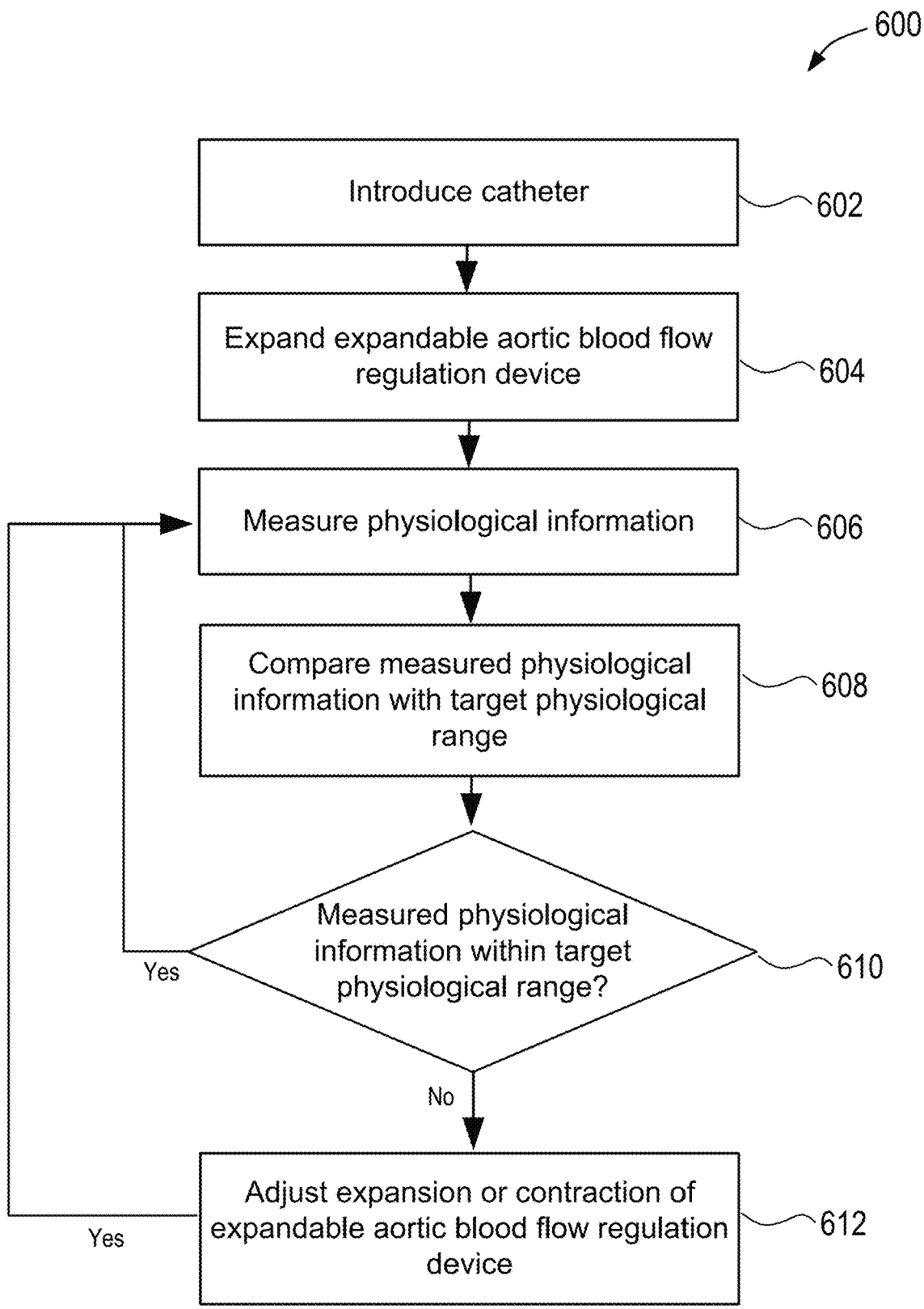
FIG. 6 is a flow chart illustrating an exemplary method for dynamically regulating the degree of aortic blood flow regulation in accordance with the principles of the present disclosure.

Referring to FIG. 6, an exemplary method for dynamically regulating the degree of aortic blood flow regulation in accordance with the principles of the present disclosure is described. Method 300 may be used to perform partial aortic occlusion, e.g., P-REBOA, EVAC, or EPACC, on a patient, for example, in shock from sepsis or trauma. At step 602, a distal end of the catheter is introduced into the patient via the femoral artery or the radial artery such that expandable blood flow regulation device 200 disposed at the distal end is placed within the aorta. As described above, expandable blood flow regulation device 200 may comprise balloon catheter 200.

At step 604, expandable blood flow regulation device 200 may be expanded to regulate blood flow through the aorta. For example, drive mechanism 408 of catheter controller unit 400 may cause balloon 204 of balloon catheter 200 to be inflated such that it regulates blood flow in the aorta.

At step 606, sensors 300 may measure physiological information indicative of blood flow through the aorta. For example, as described above, sensors 300 may measure information indicative of blood pressure distal to the expandable blood flow regulation device, blood pressure proximal to the expandable blood flow regulation device, pressure within the expandable blood flow regulation device, heart rate, respiratory rate, aortic blood flow proximal or distal to the expandable blood flow regulation device, blood temperature, cardiac output of the patient, carotid blood flow, pulmonary pressures, peripheral vascular resistance, or intracranial pressure. Sensors 300 may comprise one or more sensors positioned proximal and/or distal to expandable blood flow regulation device 200 to effectively monitor patient physiology. For example, one sensor may be positioned distal to the expandable blood flow regulation device to measure blood pressure distal to the expandable blood flow regulation device, and another sensor may be positioned proximal to the expandable blood flow regulation device to measure blood pressure proximal to the expandable blood flow regulation device.

At step 608, processor 402 of catheter controller unit 400, or when external central processing unit 500 is utilized, processor 802, may compare the measured physiological information with a target physiological range. At step 608, processor 402 may first estimate, e.g., aortic blood flow, from the measured physiological information, e.g., blood pressure distal and proximal to the expandable blood flow regulation device and corresponding waveforms, then compare the estimated aortic blood flow with a target physiological range, e.g., target aortic blood flow. At step 610, processor 402 determines whether the measured physiological information falls within the target physiological range. If it is determined at step 610 that the measured physiological information falls within the target physiological range, method 300 may maintain the current state of expansion of expandable blood flow regulation device 200 and return to step 606 to continue measuring physiological information of the patient. If it is determined at step 610 that the measured physiological information falls outside the target physiological range, e.g., exceeds or falls below the target physiological range, processor 402 of catheter controller until 400 may determine the amount of change in expansion of expandable blood flow regulation device 200 necessary to bring patient physiology within the target physiological range.

At step 612, processor 402 causes drive mechanism 408 to adjust the expansion or contraction of the expandable blood flow regulation device, e.g., inflate or deflate balloon, to adjust the amount of blood flow through the aorta. In one embodiment, drive mechanism 408 automatically adjusts the expansion or contraction of the expandable blood flow regulation device based on the amount of change in expansion of expandable blood flow regulation device 200 necessary to bring patient physiology within the target physiological range determined by processor 402. In another embodiment, at step 612, processor 402 may generate decision support that may be used by a user to enter user input such that processor 402 causes drive mechanism 408 to adjust the expansion or contraction of the expandable blood flow regulation device based on the user input. During step 612, processor 402 may generate an alert if it is determined at step 610 that the measured physiological information falls outside the target physiological range, and cause graphical user interface to communicate the alert to a user, e.g., visually or audibly.

When external central processing unit 500 is utilized, processor 502 transmits informative indicative of the amount of change in expansion of expandable blood flow regulation device 200 necessary to bring patient physiology within the target physiological range, determined at step 610, to catheter controller unit 400 via communication circuitry 506 and 406 before proceeding to step 612.

Study #1 Comparing EVAC Syringe Pump with Manual Control Pump

The following experimental study involving in vivo animal testing of a custom-built hardware and software system to control aortic flow was approved by the Institutional Animal Care and Use Committee at David Grant Medical Center, Travis Air Force Base, California. Healthy adult, castrate male and non-pregnant female Yorkshire-cross swine (Sus scrofa) were acclimated for a minimum of seven days. At the time of experimentation, animals weighed between 60 and 95 kg.

The novel components of this platform include a precision automated syringe pump coupled with a custom microcontroller that integrates streaming physiologic data from the patient. In brief, the hardware architecture utilizes a commercially available microcontroller (available from Arduino, Somerville, MA) with wireless functionality and a multi-channel 16-bit analog-to-digital converter for acquisition of real-time physiologic data including aortic flow, proximal arterial pressure, and distal arterial pressure. The custom syringe pump utilized a NEMA 17 stepper motor that drives a standard lead screw, a commercially available stepper motor controller (BigEasyDriver, available from Sparkfun, Niwot, CO), custom 3D-printed components that hold the syringe and plunger, and a wireless microcontroller that performs bidirectional communication with the master controller unit. Custom software was developed to precisely regulate aortic flow using a closed loop feedback algorithm.

A weight-based aortic flow rate of 4.3 mL/kg/min was established, which is approximately 10% of baseline distal aortic flow.

Animals were premedicated with 6.6 mg/kg intramuscular tiletamine/zolazepam (TELAZOL, available from Fort Dodge Animal Health, Fort Dodge, IA). Following isoflurane induction and endotracheal intubation, general anesthesia was maintained with 2% isoflurane in 100% oxygen. To offset the vasodilatory effects of general anesthesia, an intravenous infusion of norepinephrine (0.01 mg/kg/min) was instituted upon venous access and titrated prior to experimentation to achieve a target mean arterial pressure between 65 and 75 mm Hg. Animals were mechanically ventilated to maintain end-tidal CO2 at 40±5 mm Hg. Plasmalyte (available from Baxter, Deerfield, IL) maintenance intravenous fluid was administered at a rate of 10 mL/kg/h until the abdomen was closed, at which point the rate was decreased to 5 mL/kg/h for the remainder of the study to overcome insensible losses. Intravenous heparin was administered to achieve an activated clotting time (ACT) of 100 seconds, similar to human baseline values. An underbody warmer was used to maintain core body temperature between 35 and 37° C.

Following laparotomy, a splenectomy was performed to minimize hemodynamic variation from autotransfusion. The supraceliac aorta was exposed by dividing the left diaphragm and dissected circumferentially for a length of 5-10 cm. A perivascular aortic flow probe (available from Transonic Systems Inc., Ithaca, NY) was placed with ligation of two adjacent intercostal arteries distally, thus preventing intervening flow between the flow probe and the endovascular occlusion balloon. The abdomen was closed with cable ties. External jugular veins were cannulated to facilitate medication and fluid administration. The right brachial artery was exposed and cannulated with a 7F sheath (SuperSheath, available from Boston Scientific, Marlborough, MA) for controlled hemorrhage. The left axillary artery was exposed and cannulated with a 9F sheath (SuperSheath, available from Boston Scientific, Marlborough, MA) for proximal arterial pressure monitoring. The left femoral artery was exposed and cannulated with a 12F sheath, available from Teleflex Inc., Wayne, PA), through which an 9F Coda LP balloon (available from Cook Medical, Bloomington, IN) advanced under fluoroscopic guidance to the level of the supraceliac aorta (Zone 1), just distal to the aortic flow probe. Distal pressure was also monitored via this sheath.

Physiologic parameters and aortic flow measurements were collected in real time using a Biopac MP150 multi-channel data acquisition system and the custom Arduino-based data acquisition system/controller (available from BioPac, Goleta, CA). Parameters measured included heart rate, blood pressure proximal and distal to the intra-aortic balloons, and aortic flow beyond the Zone 1 balloon.

Data analysis was performed and graphs constructed using Excel (available from Microsoft Corporation, Redmond, WA), and STATA version 14.0 (available from Stata Corporation, Bryan, TX). Continuous variables are graphically presented as means and standard error of the means. Categorical variables are presented as means with standard deviation and standard error of the means.

At the beginning of experimentation (TO), animals were subjected to a 25% total blood volume hemorrhage over 30 minutes. Following this 30-minute hemorrhage interval, the master controller initiated stepwise balloon inflation over approximately 3 minutes until the target weight-based flow rate was achieved. The EVAC syringe pump automatically adjusted the balloon volume to actively maintain aortic flow at this level for the duration of the 45-minute EVAC interval. To ascertain the performance of the EVAC syringe pump during active resuscitation, whole blood transfusion was initiated at T65. The EVAC syringe pump then initiated a 5-minute balloon deflation and weaning sequence, beginning at T75.

Figure 7A:
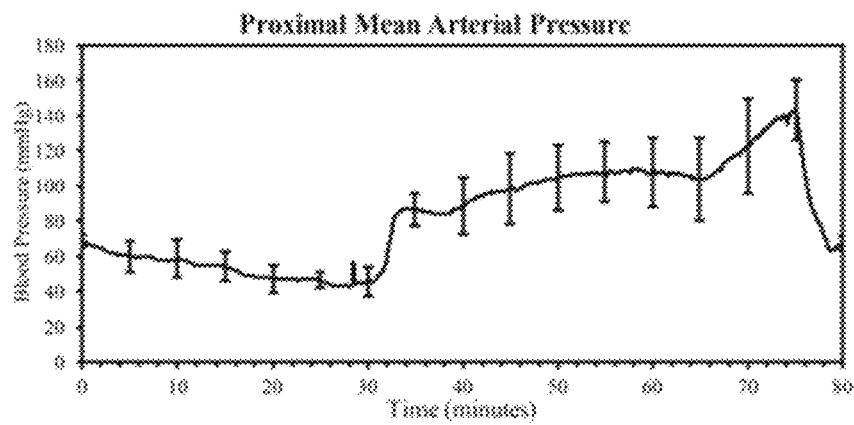
FIGS. 7A-C are graphs illustrating change in proximal mean arterial pressure, distal mean arterial pressure, and aortic flow, respectively, of a study in accordance with the principles of the present disclosure.
Figure 7B:
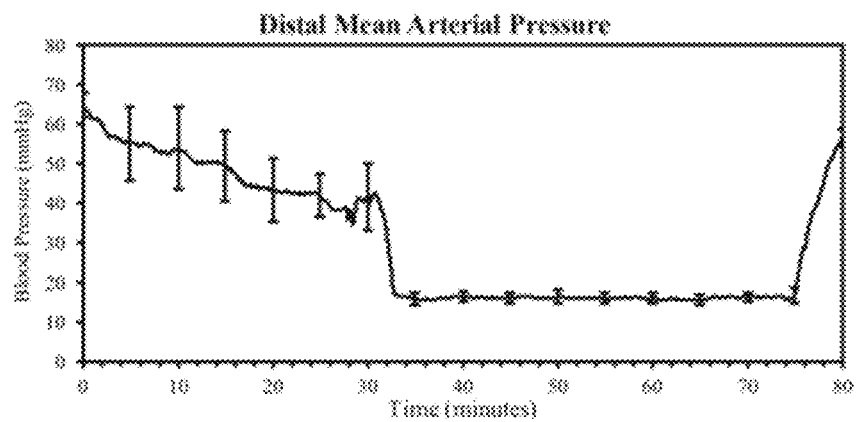
Figure 7C:
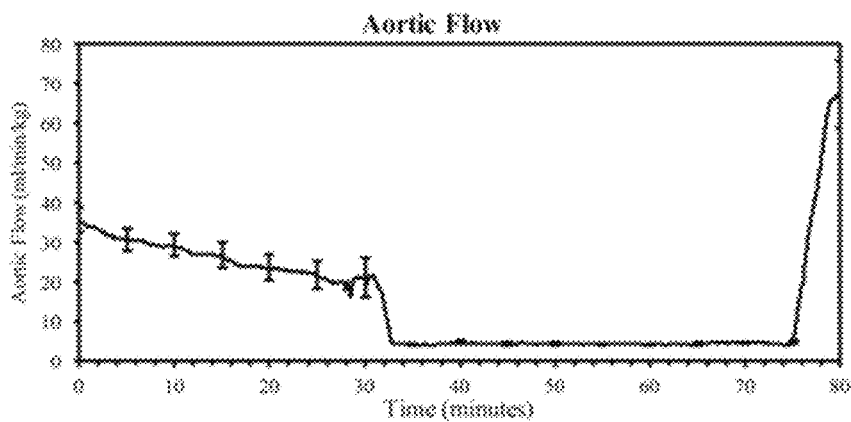

Five animals underwent instrumentation, hemorrhage, and a subsequent 45 minutes of Zone 1 EVAC. All animals survived the experimental phase. As shown in FIGS. 7A-C, hemorrhage was associated with an anticipated decline in distal aortic flow and in mean arterial pressure as measured in both the proximal descending thoracic aorta and the distal abdominal aorta, e.g., proximal MAP and distal MAP. Upon initiation of EVAC at T30, there was an abrupt increase in proximal mean arterial pressure and a concurrent decrease in distal MAP. As shown in FIG. 7B, distal aortic pressure also remained stable throughout EVAC, at approximately 16 mmHg. Referring now to FIGS. 7C, 8C, and 8D, the EVAC syringe pump was able to maintain stable aortic flow throughout the 45-minute intervention period with minimal deviation from the aortic flow goal.

Figure 8A:
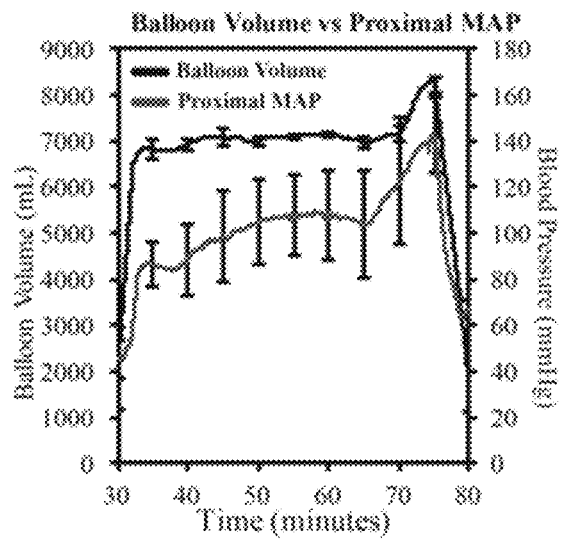
FIGS. 8A-C illustrate the relationship between balloon volume and various hemodynamic parameters in a study in accordance with the principles of the present disclosure.
Figure 8B:
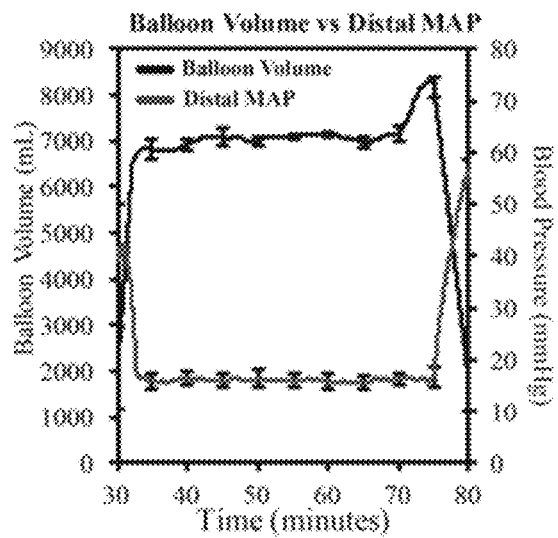
Figure 8C:
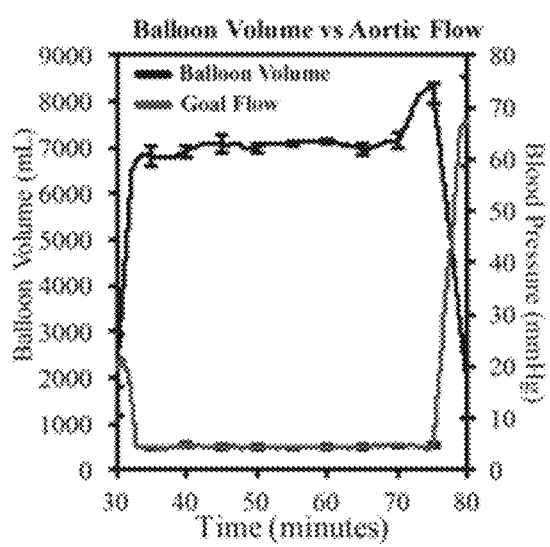
Figure 8D:
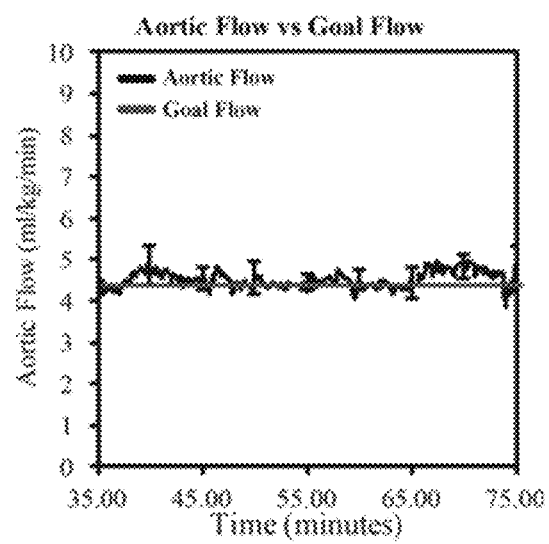
FIG. 8D illustrates the relationship between aortic flow and goal aortic flow in a study.

As shown in FIG. 8A, upon initiation of blood transfusion at T65, there was a steep rise in proximal MAP. The EVAC syringe pump responded with compensatory increase in balloon volume in order to maintain the specified aortic flow rate. Both aortic flow and distal aortic pressure remained stable and unchanged during active volume resuscitation as a result of these compensatory balloon adjustments.

Figure 9A:
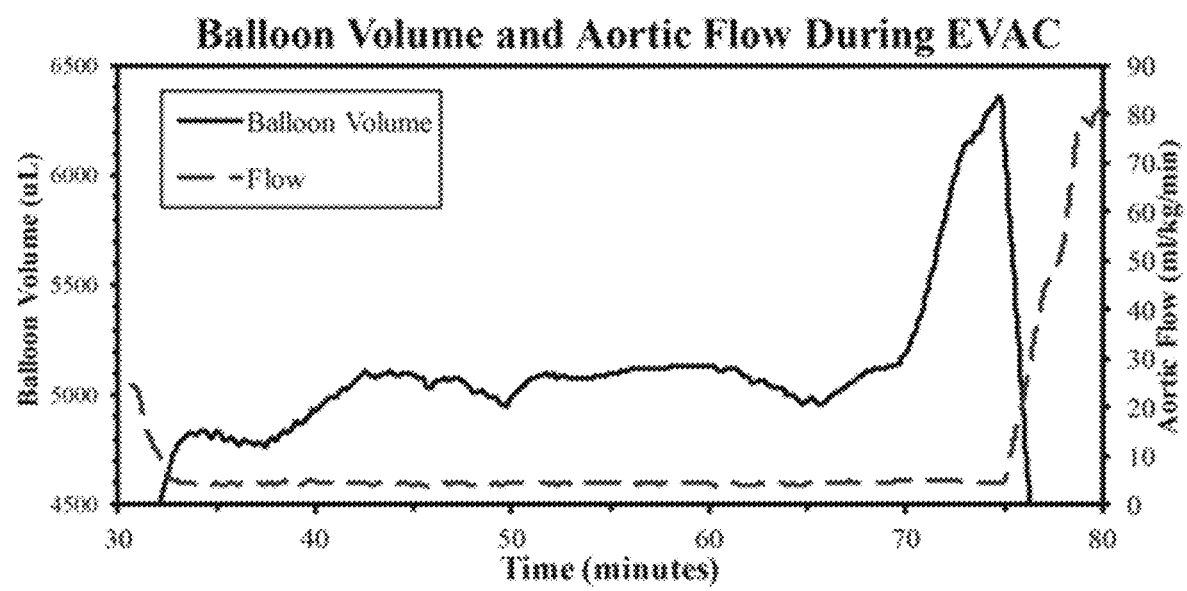
FIG. 9A illustrates the relationship between balloon volume and aortic flow during EVAC.
Figure 9B:
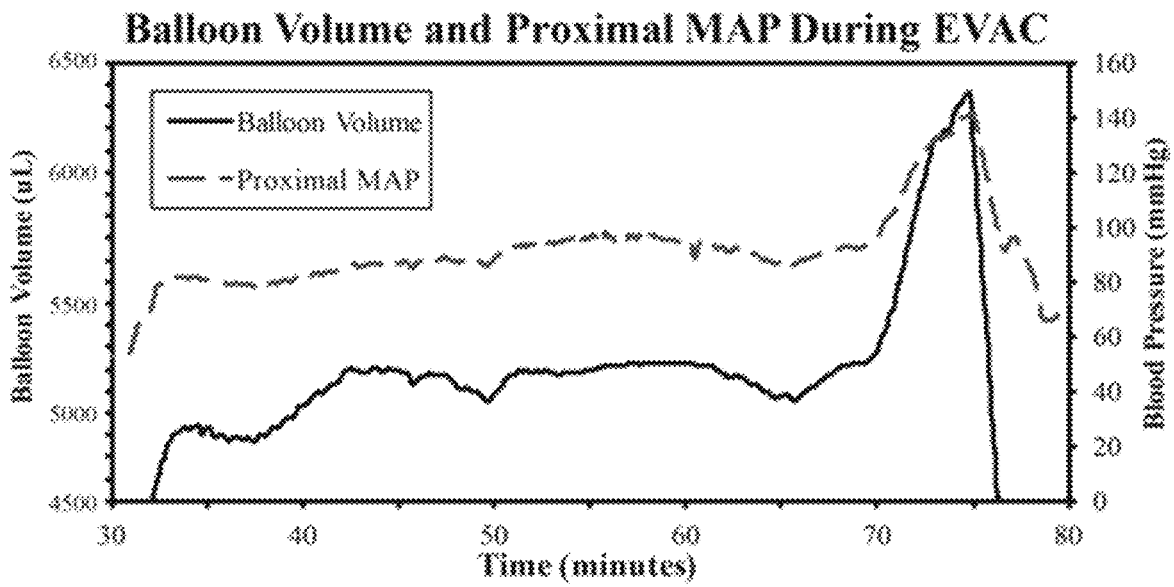
FIG. 9B illustrates the relationship between balloon volume and proximal mean arterial pressure during EVAC.

The relationship of balloon volume and the various hemodynamic parameters is represented in FIGS. 9A and 9B. The EVAC syringe pump made small, yet discernible changes in balloon volume throughout the EVAC interval, while the largest changes occurred during the 10-minute period of blood transfusion. Actual aortic flow closely approximated the target aortic flow (mean flow, 4.5 vs 4.4 ml/kg/min). As shown in FIGS. 8D and 9A, the EVAC syringe pump maintained aortic flow within 11%-14% of baseline throughout the entirety of the intervention period and between 13%-14% for greater than 90% of the intervention.

Stepwise balloon deflation resulted in a rapid, steep increase in aortic flow around the balloon. As shown in FIG. 9A, return to full baseline flow rates was observed following withdrawal of 2.5 mL from the balloon, with nearly twice baseline flow observed upon full balloon deflation (34 ml/kg/min and 67 ml/kg/min, respectively).

Throughout the 45-minute period of EVAC, the syringe pump made an average of 537 balloon adjustments, with a mean balloon volume change of 6.4 uL per adjustment. As shown in Table 1 below, the largest average balloon volume change required in order to maintain flow within the specified range was approximately 100 uL.

TABLE 1

|  | Average | Standard Deviation | SEM |
| --- | --- | --- | --- |
| Total Volume Moved (µL) | 3490.8 | 1575.1 | 643.0 |
| Total # Movements | 537 | 33 | 14 |
| Largest Volume Change (µL) | 98.7 | 101.5 | 41.4 |
| Average Volume Change (µL) | 6.4 | 2.5 | 1.0 |

FIGS. 9A and 9B demonstrate the EVAC syringe pump's control of balloon volume in response to aortic flow and proximal mean arterial pressure, respectively, for a single representative experiment. Flow remains essentially unchanged over time as a result of small, highly dynamic adjustments to balloon volume. Of note, the profile of balloon volume closely mirrors the trend in proximal mean arterial pressure throughout the intervention.

This study is the first-in-animal experience with EVAC using commercially available aortic occlusion catheters and an entirely automated flow regulating device. Precision aortic flow regulation was demonstrated to be feasible and imminently achievable with commercially available aortic occlusion catheters by adjusting occlusion balloon volumes with an algorithm-driven, autonomous syringe pump.

Early clinical experiences have demonstrated that P-REBOA is extremely challenging and results in labile hemodynamics due to the lack of fidelity with manual balloon titration. Additionally, large animal models of P-REBOA have demonstrated a tendency towards perpetuating ongoing hemorrhage. Continued bleeding is a serious concern in every clinical environment, but especially in scenarios where blood products are in limited supply or when a significant delay to surgical hemostasis is anticipated.

Thus, automation was to improve upon the P-REBOA concept. The use of automation addresses several key limitations of the manual approach to aortic flow regulation. First, the EVAC syringe pump is capable of executing very small changes in balloon filling volume. The current hardware design of the syringe pump is capable of delivering or withdrawing 10 uL aliquots of fluid at a time. These changes are too precise to be performed manually with any manner of fidelity or consistency and demand robotic control. As demonstrated in prior experiments and again in the present experiment, very small adjustments in occlusion balloon volume translate into large variations in aortic flow rate. This hyperemic aortic flow was observed during the balloon deflation phase of the experiment and likely arises from the combination of the extreme proximal aortic pressure in combination with maximally vasodilated distal tissue beds. This hyperemic flow is fairly unpredictable in its onset and occurs at different balloon volumes depending on the individual animal. Therefore, precise control is necessary to prevent hemodynamic collapse or precipitate clot destabilization and renewed hemorrhage. With balloon volume changes of as little at 10 uL producing demonstrable differences in aortic flow rates, it is apparent why previous attempts at manual flow titration have resulted in erratic hemodynamics.

Additionally, this EVAC syringe pump is capable of dynamic changes in response to changing patient physiology with near continuous adjustments of balloon volume. In the present study, there were an average of nearly 600 balloon adjustments made over a 45-minute period to maintain the desired aortic flow rate. This frequency of adjustments would be difficult, if not impossible, to achieve with manual control of the balloon volume. Moreover, humans are highly inefficient at integrating multiple streams of continuous data and responding in a timely fashion with an appropriate, measured response. Yet, computers and robots excel at these integration and computation tasks. Inefficiencies in care are compounded by assigning a skilled medical provider the sole task of manually titrating an occlusion balloon. This potential misallocation of key medical expertise and manpower may prevent the adoption of partial aortic occlusion as a resuscitation adjunct in austere environments.

In comparison to previous extracorporeal flow regulation circuits, the current EVAC syringe pump provides an equivalent, if not superior, degree of aortic flow control.

With earlier approaches, tight regulation of low volume distal aortic flow was demonstrated to effectively mitigate the ischemic burden of sustained aortic occlusion, while simultaneously minimizing hemorrhage. However, one key consideration of this current software design is that titration is predicated on aortic flow data input. Experimentally, this data was acquired through the use of a surgically implanted perivascular flow probe, which is clinically impractical. Unfortunately, there is no commercially available method of obtaining an accurate measure of aortic flow with a minimally invasive or endovascular means to enable careful titration of a balloon catheter. Despite this fact, this study does demonstrate that distal aortic pressure and aortic flow do correlate in this particular model of hemorrhage and ischemia. Therefore, it is conceivable that titrating the degree of occlusion to a specific distal aortic pressure would result in a stable downstream aortic flow.

Study #2 Comparing EVAC and REBOA

Figure 10:
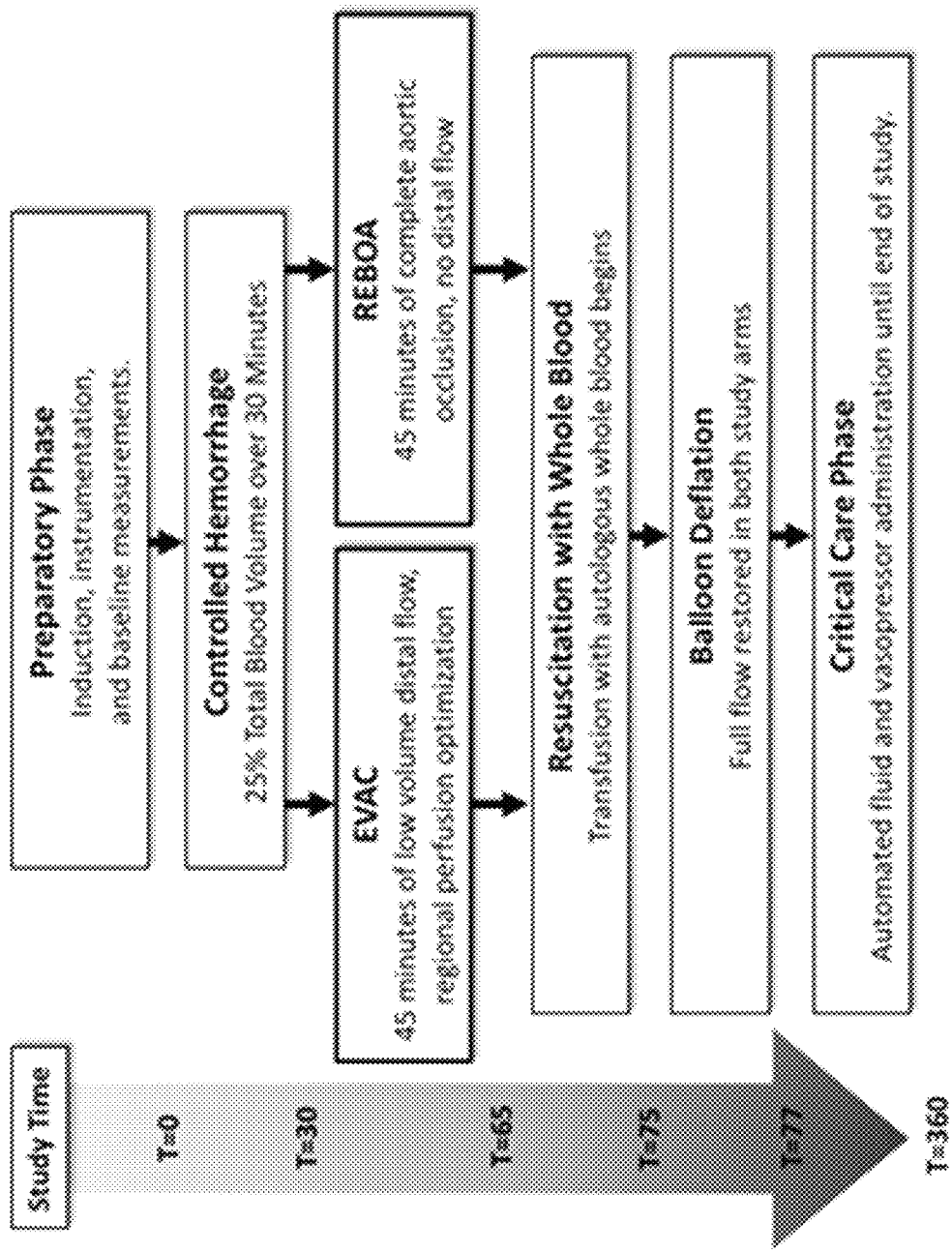
FIG. 10 is a flow chart illustrating a study in accordance with the principles of the present disclosure.

The following study comparing EVAC and REBOA was approved by The Institutional Animal Care and Use Committee at David Grant Medical Center, Travis Air Force Base. Referring now to FIG. 10, in this study, healthy adult, castrate male and non-pregnant female Yorkshire-cross swine (Sus scrofa) weighing between 60 and 95 kg were subjected to a 25% total blood volume hemorrhage over 30 minutes, followed by block randomization to a 45 minute intervention with either Zone 1 or EVAC (n=6 per group) All animals then underwent resuscitation with shed blood and received protocolized critical care phase for the remainder of a 360 minute time period, during which vasopressor and isotonic fluid administration were automatically regulated based upon predefined physiologic parameters.

Animals were premedicated with 6.6 mg/kg intramuscular tiletamine/zolazepam (TELAZOL, available from Fort Dodge Animal Health, Fort Dodge, IA). Following isoflurane induction and endotracheal intubation, general anesthesia was maintained with 2% isoflurane in 100% oxygen which was titrated to 40% oxygen to maintain a pulse oximetry between 92-98%. To offset the vasodilatory effects of general anesthesia, an intravenous infusion of norepinephrine (0.01 mg/kg/min) was instituted upon venous access, and titrated prior to experimentation to achieve a target mean arterial pressure (MAP) between 65 and 75 mm Hg. Animals were mechanically ventilated to maintain end-tidal $CO_2$ at 40±5 mm Hg. All animals received a bolus of 1 L Plasmalyte-A (available from Baxter, Deerfield, IL) upon venous access. Following the bolus, Plasmalyte-A maintenance intravenous fluid was administered at a rate of 10 mL/kg/h until the abdomen was closed, after which it was decreased to 5 mL/kg/h for the remainder of the study. Intravenous heparin was administered prior to experimentation to achieve an activated clotting time (ACT) of 100 seconds. An underbody warmer was used to maintain core body temperature between 35 and 37° C.

Following laparotomy, splenectomy was performed to minimize hemodynamic variation from autotransfusion. The supraceliac aorta was exposed by dividing the left diaphragm followed by circumferential dissection of the aorta for a length of 5-10 cm. Two adjacent intercostal arteries were ligated and a perivascular aortic flow probe (available from Transonic Systems Inc., Ithaca, NY) was placed proximal to the ligated vessels preventing intervening flow between the flow probe and the endovascular occlusion balloon. The abdomen was closed with cable ties, and vascular access was performed as previously described. A 9F Coda LP balloon (available from Cook Medial LLC, Bloomington, IN) was positioned just distal to the aortic flow probe. The inflation syringe was connected to a custom-developed EVAC automated syringe pump capable of both complete REBOA or EVAC.

Following hemorrhage and subsequent randomization, animals in the EVAC arm had tightly controlled aortic flow below the balloon for 45 minutes, ranging from 1.5 to 4.4 ml/kg/min, e.g., 100 ml/min to 300 ml/min for a 70 kg animal, achieved using a wireless automated syringe pump running custom closed loop feedback algorithms. In the REBOA arm, animals were subjected to 45 minutes of sustained complete aortic occlusion, which was maintained with the same automated syringe pump.

Beginning at 80 minutes through end of study, the administration of intravenous crystalloid fluid boluses and the titration of vasopressors was automated using a microcontroller interfaced with a standard peristaltic fluid pump and a custom infusion syringe pump, respectively. Fluid boluses were triggered based on continuous central venous pressure (CVP) and MAP values. Vasopressors were titrated up or down in response to hypotension (MAP<60) or hypertension (MAP>70), respectively. Animals were euthanized at T360, followed promptly by necropsy.

During the study, physiologic parameters and aortic flow measurements were collected in real time using a multichannel data acquisition system (Biopac MP150, available from BioPac, Goleta, CA). Parameters measured included heart rate, blood pressure proximal and distal to the intraaortic balloon catheters, central venous pressure, core temperature, and aortic flow. Arterial blood and urine were collected at routine intervals throughout the study for analysis. End-organ histology was performed and analyzed by a blinded veterinary pathologist. Data analysis was performed with STATA version 14.0 (available from Stata Corporation, Bryan, TX). Continuous variables are presented as means and standard errors of the mean if normally distributed and as medians with interquartile ranges if not distributed normally and analyzed using the appropriate test. Dichotomous and categorical variables were analyzed by Fisher's exact test and presented as percentages. Statistical significance was set at $p<0.05$.

As shown in Table 2 below, there were no differences in baseline characteristic across groups, including hemodynamics, laboratory parameters, and baseline vasopressor requirements.

TABLE 2

|  | REBOA (n = 6) | EVAC (n = 6) | p-value |
|---|---|---|---|
| Sex |  |  | 1.0 |
| Male | 4 (66.7) | 4 (66.7) |  |
| Female | 2 (33.3) | 2 (33.3) |  |
| Weight | 77.5 (8.0) | 82.5 (4.4) | 0.21 |
| pH | 7.4 (0.0) | 7.4 (0.0) | 0.59 |
| P:F | 373 (96) | 338 (74) | 0.50 |
| Hgb | 10.3 (0.8) | 11.0 (0.09) | 0.18 |
| WBC | 15.2 (3.0) | 15.4 (1.9) | 0.91 |
| Plt | 275 (45) | 183 (35) | 0.75 |
| K+ | 3.7 (0.2) | 3.7 (0.2) | 0.99 |
| Lactate | 2.4 (0.5) | 2.9 (0.6) | 0.20 |
| Creatinine | 1.3 (0.13) | 1.5 (0.2) | 0.08 |
| Glucose | 93 (8) | 87 (19) | 0.47 |
| Proximal MAP | 66 (7) | 70 (8) | 0.44 |
| Aortic Flow (ml/kg) | 38.3 (4.9) | 35.7 (3.8) | 0.37 |

Figure 11A:
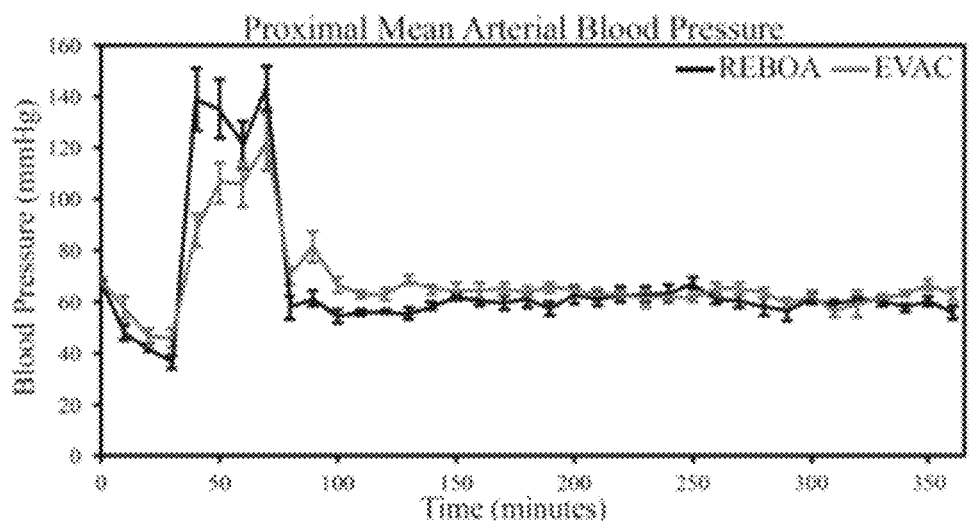
FIGS. 11A-C are graphs comparing proximal mean arterial pressures, distal mean arterial pressures, and aortic blood flow, respectively, in a study during REBOA and EVAC.
Figure 11B:
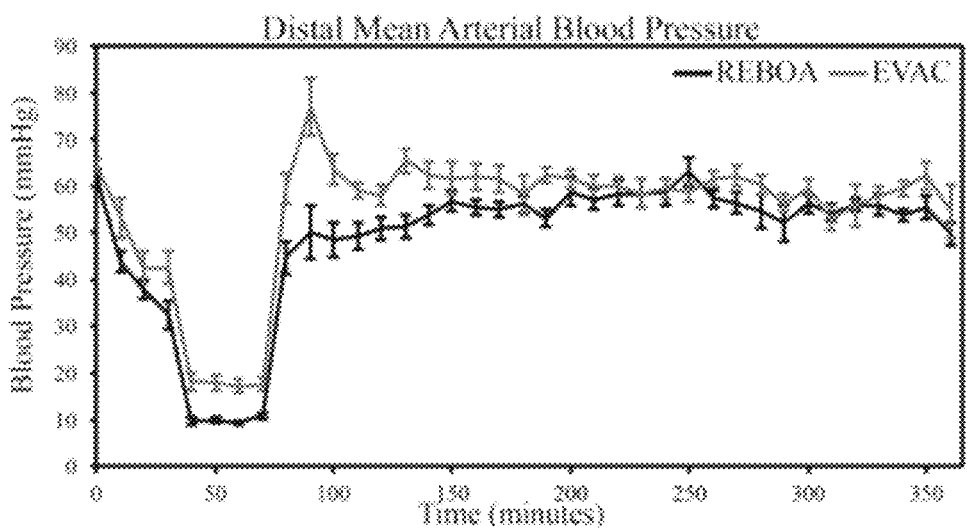
Figure 11C:
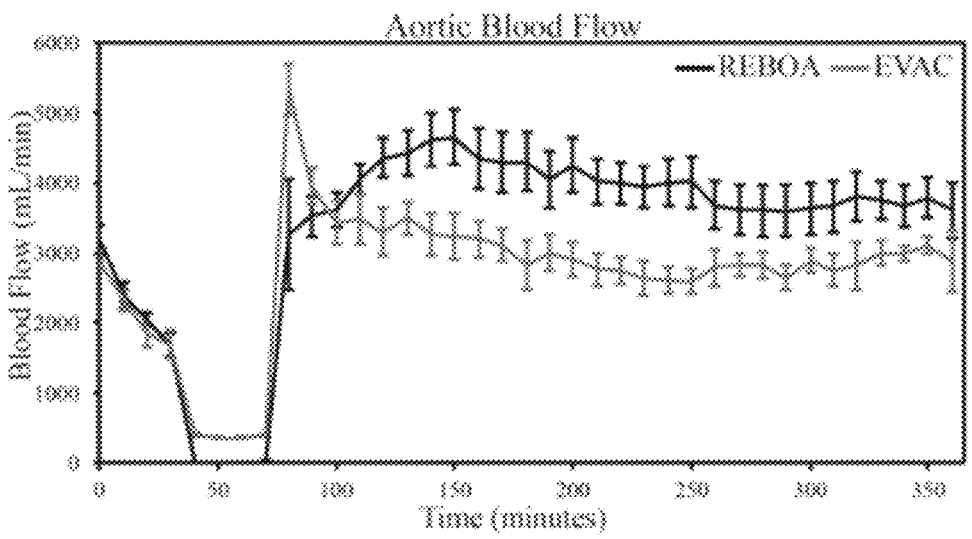

Referring now to FIGS. 11A-C REBOA and EVAC animals had a similar hypotensive response to hemorrhage (33 mmHg 95CI 29-36 vs 38 mmHg 95CI 32-44 respectively, p=0.08).

As shown in Table 3 below, during intervention, REBOA animals had significantly higher proximal MAP as compared to EVAC (129 mmHg 95CI 105-151 vs 101 mmHg 95CI 83-119 respectively, p=0.04), however there was no difference in peak MAP across the two groups. There was no appreciable flow beyond the balloon in the REBOA arm during intervention, whereas EVAC animals had a mean flow of 5.2 mL/kg/min 95CI 4.86-5.62.

TABLE 3

|  | REBOA (n = 6) | EVAC (n = 6) | p-value |
| --- | --- | --- | --- |
| Lowest pMAP—Hemorrhage Phase mmHg (SEM) | 33 (29-36) | 38 (32-44) | 0.06 |
| Average pMAP—Intervention Phase mmHg (SEM) | 129 (105-151) | 101 (83-119) | 0.04 |
| Maximum pMAP—Intervention Phase mmHg (SEM) | 161 (141-182) | 144 (125-162) | 0.13 |
| Average pMAP—Critical Care Phase mmHg (SEM) | 60 (57-63) | 64 (62-67) | 0.02 |
| Average dMAP—Critical Care Phase mmHg (SEM) | 55 (51-59) | 61 (57-64) | 0.02 |
| Average Aortic Flow—Critical CarePhase ml/min (SEM) | 3960 (3176-4743) | 3028 (2458-3598) | 0.03 |
| Average Aortic Flow—Critical Care Phase ml/kg/min (SEM) | 51 (41-61) | 36 (30-44) | 0.01 |
| Urine Output—Total ml/kg (SEM) | 40 (32-48) | 23 (20-26) | 0.08 |
| Serum Creatinine—Final | 1.68 (1.56-1.80) | 1.66 (1.63-1.69) |  | pMAP = proximal mean arterial pressure;

During the critical care phase, EVAC animals maintained an average proximal MAP within the goal range and had a higher overall MAP throughout this time period than REBOA animals. EVAC animals also demonstrated aortic flow rates closer to baseline values during critical care as compared to REBOA animals (36 ml/kg/min 95CI 30-44 vs 51 mL/kg/min 95CI 41-61, p=0.01).

Figure 12B:
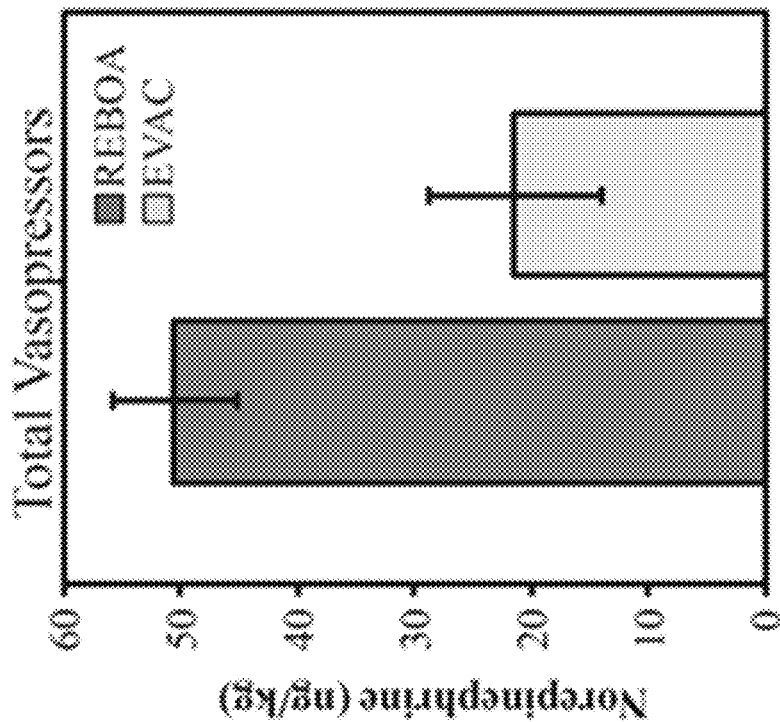
FIGS. 12A and 12B illustrate total resuscitation fluids and total vasopressors, respectively, required during REBOA and EVAC.
Figure 12A:
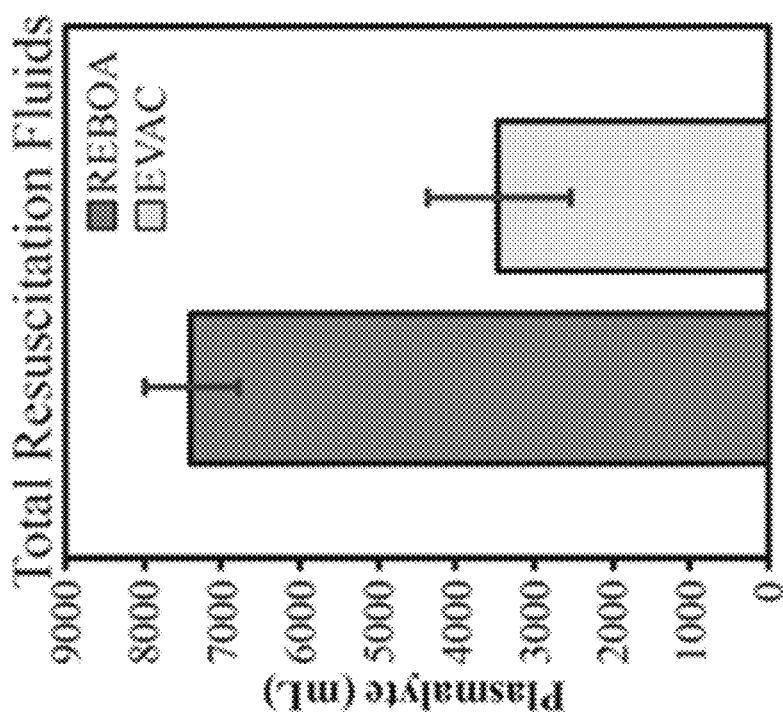

Referring now to FIGS. 12A and 12B, notable differences were seen in resuscitation requirements during the critical care phase of the experiment. In response to more frequent episodes of hypotension and low CVP, REBOA animals required more than twice the amount of crystalloid when compared to EVAC animal (7400 ml 95CI 6148-8642 vs 3450 ml 95CI 1215-5684, p<0.01). Additionally, vasopressor requirements were significantly higher in REBOA animals (50.5 ng/kg+/−5.3 vs 21.5 ng/kg+/−7.4, p=0.05).

One animal in the EVAC group experienced progressive hemodynamic deterioration during the critical care phase and died 40 minutes prior to the end of study. Overall fluid and vasopressor requirements in this animal were greater than 2 standard deviations greater than the mean fluid and vasopressor requirements for the entire EVAC cohort and 3 standard deviations compared to the 5 surviving EVAC animals. This animal was also the only animal in either group to have a baseline aortic flow below inclusion criteria prior to the initial pre-experiment fluid bolus but did meet inclusion criteria for aortic flow following fluid administration and was therefore included in the study.

Figure 13:
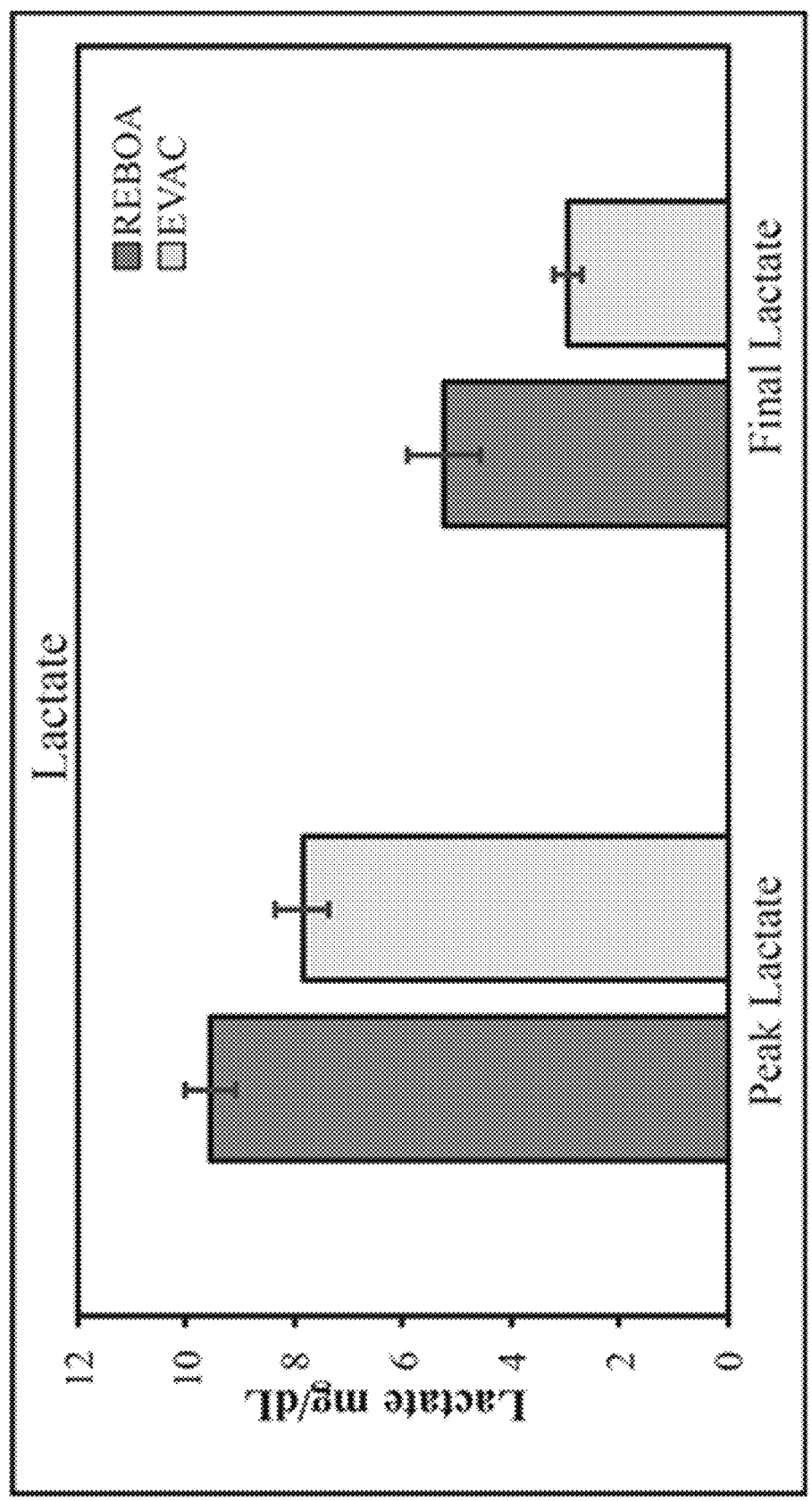
FIG. 13 illustrates the peak and final lactate levels during REBOA and EVAC.

Referring now to FIG. 13, both peak and final lactate levels were significantly lower in the EVAC group. There were no differences in hemoglobin values across groups following resuscitation, and there was no difference in final creatinine levels across groups. Histologic analysis did not reveal any significant differences between REBOA and EVAC animals.

In this large animal model of hemorrhage with a period of intervention reflective of current clinical REBOA use, EVAC resulted in less distal ischemia and physiologic derangement when compared to REBOA. This improvement is evidenced by lower levels of serum lactate and decreased resuscitation requirements during the critical care phase. Additionally, EVAC augments proximal pressure in a more physiologic manner during hemorrhagic shock, reducing the extreme blood pressures to the heart, lungs and brain that are produced by standard REBOA. These beneficial physiologic outcomes were demonstrated over the clinically relevant occlusion period of 45 minutes. Finally, this study demonstrates that carefully titrated distal aortic flow is possible by combining an automated syringe pump with a standard, currently available aortic occlusion catheter.

In a previous proof-of-concept experiment, an extracorporeal circuit was utilized to precisely control distal aortic blood flow in a porcine liver injury model, where all control animals died within minutes. An intervention period of 90 minutes was used to simulate the reality of modern tactical evacuation on the battlefield, recognizing that application of complete REBOA is not feasible in scenarios where prolonged intervention (greater than 60 minutes) is required. The degree of distal ischemia from complete aortic occlusion, e.g., REBOA, resulted in dramatic increases in mortality and resuscitation requirements compared to animals provided carefully titrated distal aortic flow. Importantly, this study demonstrated that a mere 10% of baseline aortic flow delivered by the EVAC device was sufficient to offset the deleterious effects of sustained aortic occlusion, including distal ischemia and the supraphysiologic proximal aortic pressure and cardiac afterload induced by sustained complete aortic occlusion. Additionally, this prior study demonstrated that allowing 10% distal aortic flow in the face of a devastating, uncontrolled liver injury did not create clot disruption and fatal ongoing hemorrhage. This was a striking difference from previous attempts to achieve partial aortic flow using manual titration in an analogous liver injury model, where early demise was encountered due to uncontrolled downstream blood flow and subsequent ongoing hemorrhage.

These initial experiments suggested that titrated aortic flow may be a viable approach to extend the benefits of REBOA for prolonged periods of intervention. However, these preliminary studies did not address the more commonplace scenario of in-hospital application of REBOA, where maximum occlusion time is typically limited to less than 60 minutes. For these shorter occlusion periods, no previous data exist, either clinical or translational, suggesting that a partial flow strategy would provide a physiologic benefit over complete aortic occlusion. This current study sought to address this key concern regarding the clinical applicability of EVAC in present-day scenarios. For intervention periods as short as 45 minutes, EVAC still dramatically reduced the physiologic impact of sustained aortic occlusion, resulting in a more modest physiologic proximal pressure augmentation. Following resuscitation, both fluid and vasopressor requirements were less than half that required following REBOA. Moreover, EVAC resulted in less hyperemic flow throughout the critical care phase, as evidence by lower aortic flow rates during the critical care phase. This finding likely reflects the reduced physiologic insult of this intervention. In all, the present study provides experimental support for an EVAC partial flow strategy for intervention periods reflective of typical in-hospital use.

Mounting clinical evidence suggests that applying REBOA at or after the point of cardiac arrest results in poor survival, on par with the dismal survival rates for patients undergoing resuscitative thoracotomy. Conversely, application of REBOA prior to hemodynamic collapse has been shown to result in improved survival. Therefore, intervening earlier in the course of resuscitative efforts should be a priority in the overall management of this patient population. Based on the improved ischemic profile and physiologic response delivered by EVAC, this strategy could theoretically be applied prior to the threshold at which one would utilize REBOA. Use in this fashion may not only lead to improved survival, but also favorably minimize morbidity by reducing the downstream consequences of large volume transfusions, vasopressors, and crystalloids that are well described during trauma resuscitation.

Through continued technological development, a viable strategy to achieve controlled, titrated distal aortic flow using conventional compliant balloon catheters inflated with an automated syringe pump was refined. This pump and controller represents a major advancement forward. Given the complex interplay of pressure, cardiac output, vascular tone, and other neuroendocrine factors, precision aortic flow regulation with EVAC requires automation using closed-loop feedback, where small changes in balloon volume beyond the capacity of manual control are executed in real time. The automated syringe pump utilized in this study is capable of making microliter-sized balloon volume adjustments in a near continuous fashion. The development of this experimental EVAC syringe pump advances the field closer to a clinically relevant endovascular device for the management of non-compressible truncal hemorrhage.

While the only death in this experiment was in the EVAC study arm, it is important to highlight that this animal was an outlier in the data, requiring significantly higher fluid and vasopresssor requirements by comparison. The present study was a subset of a broader study involving six randomization arms, evaluating several derivative applications of this technology. This was the only animal out of nearly sixty to not survive the duration of the study. Despite being an outlier, all physiologic and laboratory data from this animal were included in the analysis, which certainly decreases the overall differences between groups. Nonetheless, the present study demonstrated significant differences between the groups across multiple physiologic and biochemical endpoints, only strengthening the perceived benefit of EVAC compared to REBOA.

There are several limitations to the current study. First, this was a non-survival study with a total experimental time of only 6 hours. It is likely that critical differences between groups with respect to physiology or histology would manifest with studies of longer duration. Nonetheless, fidelity of the EVAC syringe pump to deliver stable aortic flow, particularly during active resuscitation with whole blood at the end of the intervention period, was on par with previous extracorporeal flow circuit models. The current hardware implementation to generate EVAC via endovascular means is experimental, with aortic flow being regulated based on direct aortic flow measurements via a perivascular probe encircling the supraceliac aorta. However, consistent with previous reports, there is a strong correlation between the distal aortic pressure and downstream aortic flow beyond the balloon, specifically at the low flow rates targeted in this study. This suggests that distal pressure may serve as a viable surrogate metric for aortic flow by which to regulate EVAC clinically. Notwithstanding these limitations, these results provide a significant advancement in technique and technology to mitigate the deleterious consequences of REBOA while maintaining the lifesaving advantages.

While various illustrative embodiments of the disclosure are described above, it will be apparent to one skilled in the art that various changes and modifications may be made therein without departing from the disclosure. The appended claims are intended to cover all such changes and modifications that fall within the true scope of the disclosure.

What is claimed:

1. A controller unit for automating expansion and contraction of an expandable blood flow regulation device, the expandable blood flow regulation device disposed at a distal region of a catheter, the controller unit comprising:
a pump in fluid communication with the expandable blood flow regulation device via the catheter, the pump configured to expand and contract the expandable blood flow regulation device;
a processor operatively coupled to one or more sensors and configured to:
receive physiological information from the one or more sensors;
compare the physiological information from the one or more sensors with a target physiological range;
calculate a dynamic scaling factor;
calculate a bolus volume based at least in part on the dynamic scaling factor; and
cause the pump to adjust expansion or contraction of the expandable blood flow regulation device by the bolus volume to adjust an amount of blood flow through a vessel if the physiological information from at least one of the one or more sensors falls outside the target physiological range.

2. The controller unit of claim 1, wherein the expandable blood flow regulation device comprises a balloon configured to be inflated to expand to restrict blood flow through the vessel, and wherein the pump is configured to inflate or deflate the balloon to adjust the amount of blood flow through the vessel if the physiological information from at least one of the one or more sensors falls outside the target physiological range.

3. The controller unit of claim 2, wherein the pump is configured to inflate or deflate the balloon by delivering bolus volumes as small as 1 microliters.

4. The controller unit of claim 2, wherein the pump is configured to inflate or deflate the balloon by delivering bolus volumes between 1 and 50 microliters.

5. The controller unit of claim 2, wherein the pump is configured to inflate or deflate the balloon via a stepper motor coupled to the processor.

6. The controller unit of claim 5, wherein the pump is a syringe pump.

7. The controller unit of claim 1, wherein the pump is configured to automatically adjust expansion or contraction of the expandable blood flow regulation device to adjust the amount of blood flow through the vessel if the physiological information from at least one of the one or more sensors falls outside the target physiological range.

8. The controller unit of claim 1, wherein the pump is configured to adjust expansion or contraction of the expandable blood flow regulation device to adjust the amount of blood flow through the vessel if the physiological information from at least one of the one or more sensors falls outside the target physiological range based on user input.

9. The controller unit of claim 1, further comprising a graphical user interface configured to display information indicative of the comparison.

10. The controller unit of claim 9, wherein the graphical user interface is further configured to communicate decision support audibly based on the comparison such that a user may provide user input based on the decision support.

11. The controller unit of claim 1, wherein the processor generates an alert if the physiological information from at least one of the one or more sensors falls outside the target physiological range.

12. The controller unit of claim 1, wherein the one or more sensors comprises a proximal sensor positioned proximal to the expandable blood flow regulation device.

13. The controller unit of claim 1, wherein the one or more sensors comprises a distal sensor positioned distal to the expandable blood flow regulation device.

14. The controller unit of claim 1, wherein the one or more sensors comprises one or more blood pressure sensors.

15. The controller unit of claim 1, wherein the physiological information includes blood pressure waveforms.

16. The controller unit of claim 1, wherein the processor is further configured to:
prior to calculating the dynamic scaling factor, cause the pump to adjust expansion or contraction of the expandable blood flow regulation device a first time.

17. The controller unit of claim 1, wherein the processor is further configured to:
determine that a time delay has elapsed;
after causing the pump to adjust expansion or contraction of the expandable blood flow regulation device by the bolus volume and in response to determining that the time delay has elapsed, receive subsequent physiological information from the one or more sensors; and
calculate a difference between the subsequent physiological information from at least one of the one or more sensors and the target physiological range.

18. The controller unit of claim 17, wherein the bolus volume is a first bolus volume, and wherein the processor is further configured to:
modify the dynamic scaling factor based on the difference; and
calculate a second bolus volume based on the modified dynamic scaling factor.

19. The controller unit of claim 17, wherein the time delay is based on the difference.

20. A system for partial-aortic occlusion comprising:
the controller unit of claim 1; and
the expandable blood flow regulation device disposed at the distal region of the catheter; and
the one or more sensors.

21. The system of claim 20, further comprising one or more additional sensors operatively coupled to the processor and configured to measure at least one of pressure within the expandable blood flow regulation device, heart rate, respiratory rate, blood temperature, cardiac output of a patient, carotid blood flow, pulmonary pressures, peripheral vascular resistance, or intracranial pressure.

22. The system of claim 20, further comprising an external central processing unit operatively coupled to the controller unit and the one or more sensors, the external central processing unit comprising the processor and configured to transmit information indicative of whether the physiological information from at least one of the one or more sensors falls outside the target physiological range to the controller unit.

23. The system of claim 22, wherein the external central processing unit transmits the information to the controller unit via at least one of WiFi, Bluetooth, Wixel-based communication, cellular communication, or other form of communication.

24. A method for blood flow regulation comprising:
advancing a catheter comprising an expandable blood flow regulation device into a vessel of a patient;
expanding the expandable blood flow regulation device to restrict blood flow through the vessel via a catheter controller unit coupled to the catheter;
measuring physiological information via one or more sensors coupled to the catheter;
comparing the measured physiological information from the one or more sensors with a target physiological range;
calculating a dynamic scaling factor;
calculating a bolus volume based at least in part on the dynamic scaling factor; and
adjusting expansion or contraction of the expandable blood flow regulation device by the bolus volume if the measured physiological information from at least one of the one or more sensors falls outside the target physiological range.

* * * * *